United States Patent
Matthews et al.

(10) Patent No.: US 8,002,151 B2
(45) Date of Patent: Aug. 23, 2011

(54) METHOD OF PRODUCING FOAMED CLEANSER WITH SUSPENDED PARTICLES THEREIN AND A DISPENSER THEREFORE

(75) Inventors: Shaun Kerry Matthews, Lincoln (GB); Stewart Banks, Algarve (PT); Kara Catherine Stonehouse, Kanata (CA)

(73) Assignee: Deb IP Limited, Belper, Derbyshire (GB)

( * ) Notice: Subject to any disclaimer, the term of this patent is extended or adjusted under 35 U.S.C. 154(b) by 555 days.

(21) Appl. No.: 11/123,237

(22) Filed: May 6, 2005

(65) Prior Publication Data

US 2005/0258192 A1 Nov. 24, 2005

Related U.S. Application Data

(60) Provisional application No. 60/568,739, filed on May 7, 2004.

(51) Int. Cl.
*B67D 7/76* (2010.01)

(52) U.S. Cl. ............ 222/190; 222/1; 222/195; 222/137; 222/276; 222/145.5; 222/181.3; 261/DIG. 26; 239/343

(58) Field of Classification Search ................. 222/190, 222/1, 195, 134–137, 276, 630, 180–181.3, 222/145.1, 145.5; 261/DIG. 26; 239/343
See application file for complete search history.

(56) References Cited

U.S. PATENT DOCUMENTS

| | | | |
|---|---|---|---|
| 2,494,827 A | 1/1950 | Munter | |
| 3,985,271 A * | 10/1976 | Gardner | 222/190 |
| 4,051,877 A * | 10/1977 | Fletcher et al. | 141/4 |
| 4,155,870 A | 5/1979 | Jorgensen | |
| 4,615,467 A | 10/1986 | Grogan et al. | |
| 4,639,367 A | 1/1987 | Mackles | |
| 5,238,155 A * | 8/1993 | Blake, III | 222/190 |
| 5,445,288 A * | 8/1995 | Banks | 222/95 |
| 6,082,586 A * | 7/2000 | Banks | 222/95 |
| 6,271,275 B1 * | 8/2001 | Malwitz | 521/133 |
| 6,321,943 B1 * | 11/2001 | Strickler et al. | 222/82 |
| 6,394,316 B1 * | 5/2002 | Daansen | 222/207 |
| 6,699,019 B2 * | 3/2004 | Myers et al. | 417/334 |
| 6,913,251 B2 * | 7/2005 | Kerfoot | 261/77 |
| 2004/0234458 A1 * | 11/2004 | Riedel et al. | 424/47 |
| 2005/0224519 A1 * | 10/2005 | Law et al. | 222/190 |

FOREIGN PATENT DOCUMENTS

| | | |
|---|---|---|
| CA | 2 233 323 | 4/1997 |
| CA | 2 202 224 | 10/1997 |

(Continued)

*Primary Examiner* — J. Casimer Jacyna

(74) *Attorney, Agent, or Firm* — Hill & Schumacher

(57) ABSTRACT

One aspect of the invention is a foaming component for use in association with a foam dispenser. The foaming component includes an air sparging element, a mixing chamber, and an air chamber. The mixing chamber is on one side of the air sparging element and it defines a portion of the mixing chamber. The air chamber is on the other side of the air sparging element and it defines a portion of the air chamber. The air chamber has an air inlet. The mixing chamber has a liquid inlet and an outlet, and the outlet is down stream of the inlet. The foaming component also forms part of a new foam dispenser. The foaming component and the foam dispenser are for use in the production of foam with a plurality of particles suspended therein. Another aspect of the invention is a dispenser with a foaming component therein.

38 Claims, 13 Drawing Sheets

FOREIGN PATENT DOCUMENTS

| | | |
|---|---|---|
| CA | 2 276 661 | 7/1998 |
| CA | 2 244 591 | 2/1999 |
| CA | 2 333 455 | 2/1999 |
| CA | 2 447 786 | 11/2002 |
| CA | 2 465 615 | 5/2003 |
| EP | 0 829 259 | 3/1998 |
| EP | 1 169 010 | 11/2004 |
| GB | 2 335 005 | 9/1999 |
| WO | WO 94 12151 | 6/1994 |
| WO | WO 98 13144 | 4/1998 |
| WO | 99/22698 | 5/1999 |
| WO | 99/22701 | 5/1999 |
| WO | WO 01 30310 A1 | 5/2001 |
| WO | 02/092025 | 11/2002 |

\* cited by examiner

FIG 7

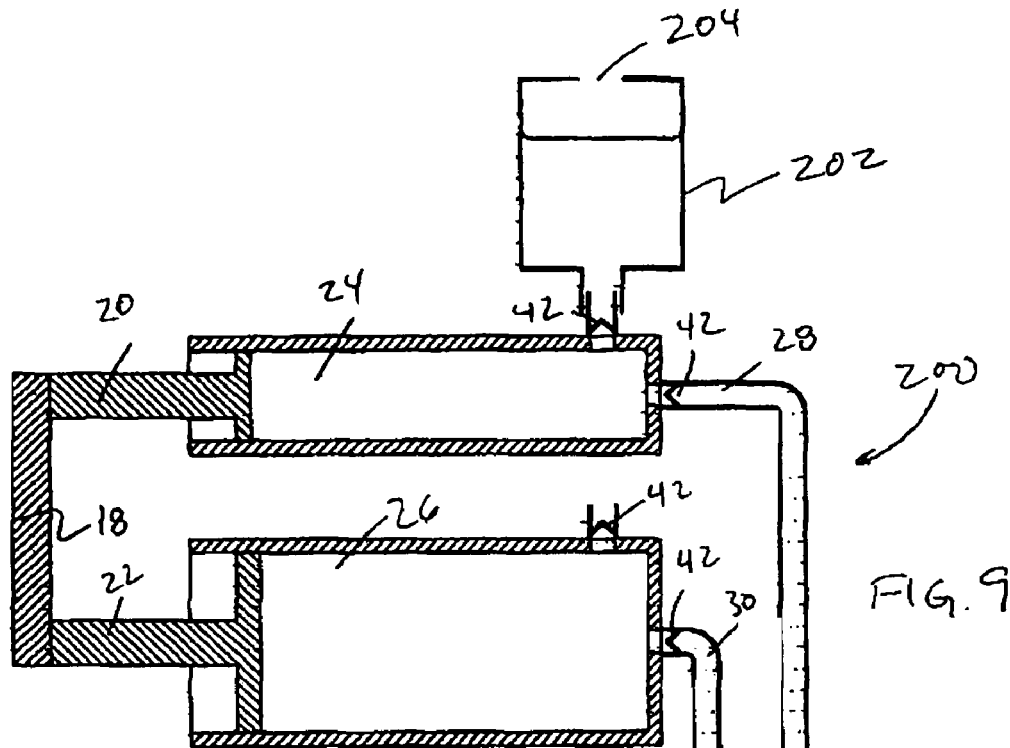
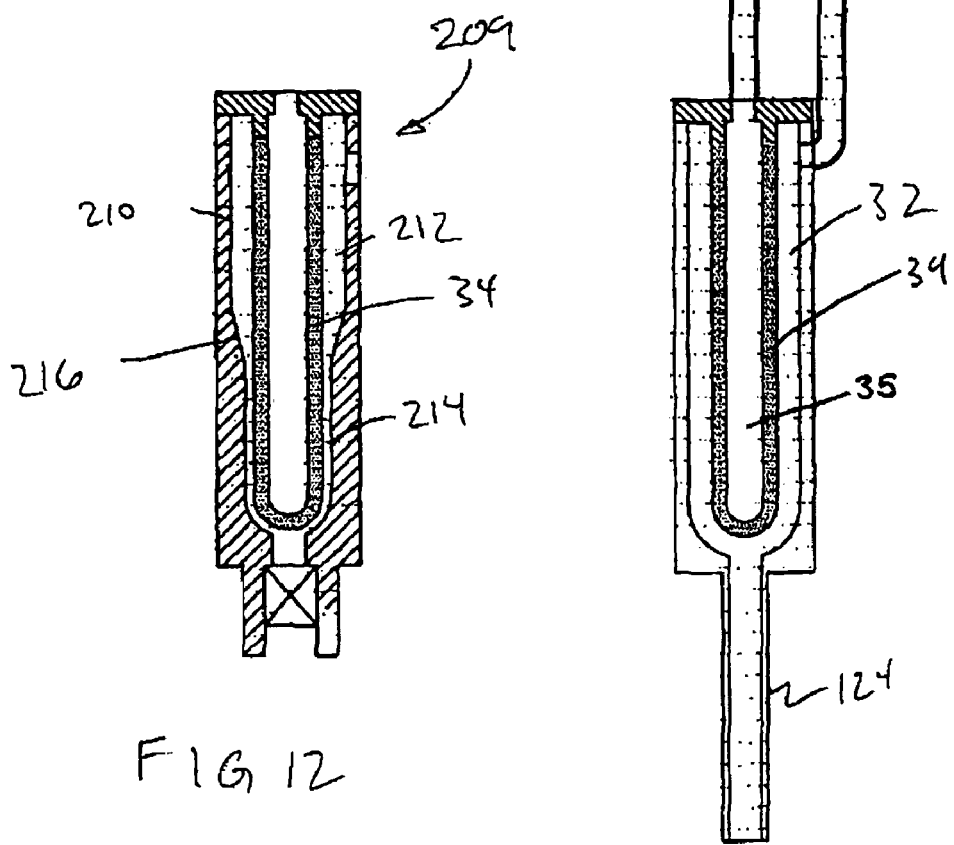
FIG. 9
FIG 12

METHOD OF PRODUCING FOAMED CLEANSER WITH SUSPENDED PARTICLES THEREIN AND A DISPENSER THEREFORE

CROSS REFERENCE TO RELATED PATENT APPLICATION

This patent application relates to U.S. Provisional Patent Application Ser. No. 60/568,739 filed on May 7, 2004 entitled FOAMED CLEANSER WITH SUSPENDED PARTICLES, A METHOD OF PRODUCING SAME AND A DISPENSER THEREFORE.

FIELD OF THE INVENTION

This invention relates to cleansers with suspended particles, a technique to produce them and dispensers for producing them and in particular to cleansers that are dispensed as foams.

BACKGROUND OF THE INVENTION

Liquid dispensers for dispensing soap and the like are well known. There are a wide variety of liquid dispensers for use in association with liquid soap. Some of these dispense the soap or other liquid in the form of foam. There are a number of advantages that are realized by dispensing in the form of foam. Specifically foam is easier to spread than the corresponding liquid. As well there is much less splashing or run-off since the foam has a much higher surface tension than the liquid. In addition, the foam requires much less liquid to produce the same cleansing power as compared to the unfoamed liquid due to the much higher surface area of the foam. Accordingly the cost to wash a specific number of hands is reduced since the amount of soap used is reduced. Similarly there are environmental benefits from using the foam since the amount of product used is reduced.

Similarly there are a number of advantages to soaps with suspended particles. This is particularly true in regard to heavily soiled skin. It is also true for more gentle cleansers that are used as exfoliating scrubs. The particles in the soap or the cleanser provide an abrasive component which enhances the cleaning abilities of the soap or cleanser. Heretofore there has not been a dispenser that would provide for foam with suspended particles wherein the advantages of the foam described above is combined with the advantages of a soap with abrasives.

Accordingly it would be advantageous to provide a foam soap with suspended particles. Further, it would be advantageous to provide a foam dispenser that dispenses a foam soap with suspended particles. Still further, it would be advantageous to provide an alternate dispenser for providing foam.

SUMMARY OF THE INVENTION

One aspect of the invention is a foaming component for use in association with a foam dispenser. The foaming component includes an air sparging element, a mixing chamber, and an air chamber. The mixing chamber is on one side of the air sparging element and the air sparging element defines a portion of the mixing chamber. The mixing chamber has a liquid inlet. The air chamber is on the other side of the air sparging element and the air sparging element defines a portion of the air chamber. The air chamber has an air inlet. The mixing chamber has an outlet and the outlet extends from the mixing chamber down stream of the liquid inlet.

In another aspect of the invention there is a new foam dispenser. The foam dispenser is for use in association with a liquid. The foam dispenser includes a liquid container, a foaming component and a pump. The foaming component includes an air sparging element, a mixing chamber, a foaming component air chamber. The mixing chamber is on one side of the air sparging element and the air sparging element defines a portion of the mixing chamber. The mixing chamber has a liquid inlet in flow communication with the liquid container. The foaming component air chamber is on the other side of the air sparging element and the air sparging element defines a portion of the air chamber. The air chamber has an air inlet. The mixing chamber has a mixing chamber outlet which is down stream of the liquid inlet. The pump is operably connected to the liquid inlet and the air inlet and is adapted to pump air into the foaming component air chamber and liquid into the mixing chamber.

In a further aspect of the invention there is provided a method of making foam. The method includes the steps of: providing air under pressure to one side of an air sparging element; providing liquid under pressure to a mixing chamber on the other side of an air sparging element; pushing the air through the sparging element into the mixing chamber, and mixing the air and the liquid thereby creating foam.

Further features of the invention will be described or will become apparent in the course of the following detailed description.

BRIEF DESCRIPTION OF THE DRAWINGS

The invention will now be described by way of example only, with reference to the accompanying drawings, in which:

FIG. 7 is a cross sectional view of a fifth embodiment of a dispenser for dispensing foam with suspended particles of the present invention having a top skimmer in the liquid container;

FIG. 9 is a cross sectional view of a seventh embodiment of the dispenser for dispensing foam with suspended particles of the present invention having a single rigid liquid container;

FIG. 12 is a cross sectional view of a second alternate foaming component of a dispenser for dispensing foam with suspended particles wherein the mixing chamber has a stepped annulus;

DETAILED DESCRIPTION OF THE INVENTION

The present invention relates to a dispenser for dispensing foam with suspended particles. Heretofore conventional non-aerosol dispensers have not been able to provide particles in foam. In conventional dispensers foam is created by mixing air and liquid and then pushing the mixture through a porous material. If particles are introduced into the liquid, the porous material would act like a sieve, the particles would be removed from the liquid, and the resulting foam would not include particles.

Accordingly to overcome the limitations of the previous foam dispensers he dispenser of the present invention uses an air sparging process in the production of foam. That is, air is introduced into the liquid through a plurality of tiny holes or an air sparging element to create foam. It will be appreciated by those skilled in the art that by using this air sparging process a wide variety of liquids can be "foamed". Thus through the use of the invention herein a foam with suspended particles may be produced.

Generally one of the limitations of a liquid with particles suspended therein is that over time the particles either float to the top or sink to the bottom of the container. Generally heavy duty cleansers overcome this limitation by adding viscosity modifiers (thickeners) to the liquid to aid in the suspension of the particles. Typically the resultant increase in viscosity prevents effective foaming behaviour. Generally liquids with viscosity greater than 100 centipose will be very poor foamers. However, liquids with highly non-Newtonian behaviour can be manufactured that exhibit viscosity at low shear rates that is sufficient to maintain the particles in evenly distributed suspension but conversely have very low viscosity when exposed to high shear rates. Thus these types of liquids would be foamable. As a result the production of a foamable heavy duty cleanser with particles suspended therein is very costly. Accordingly a dispenser for producing foam should be adaptable for use with liquids with non-newtonian behavioiur; liquids that include re-mixed particles that have either settled to the bottom or floated to the top; or a mixture of different liquids. Set out below are different embodiments, each of which addresses one of these challenges.

Figure 1:
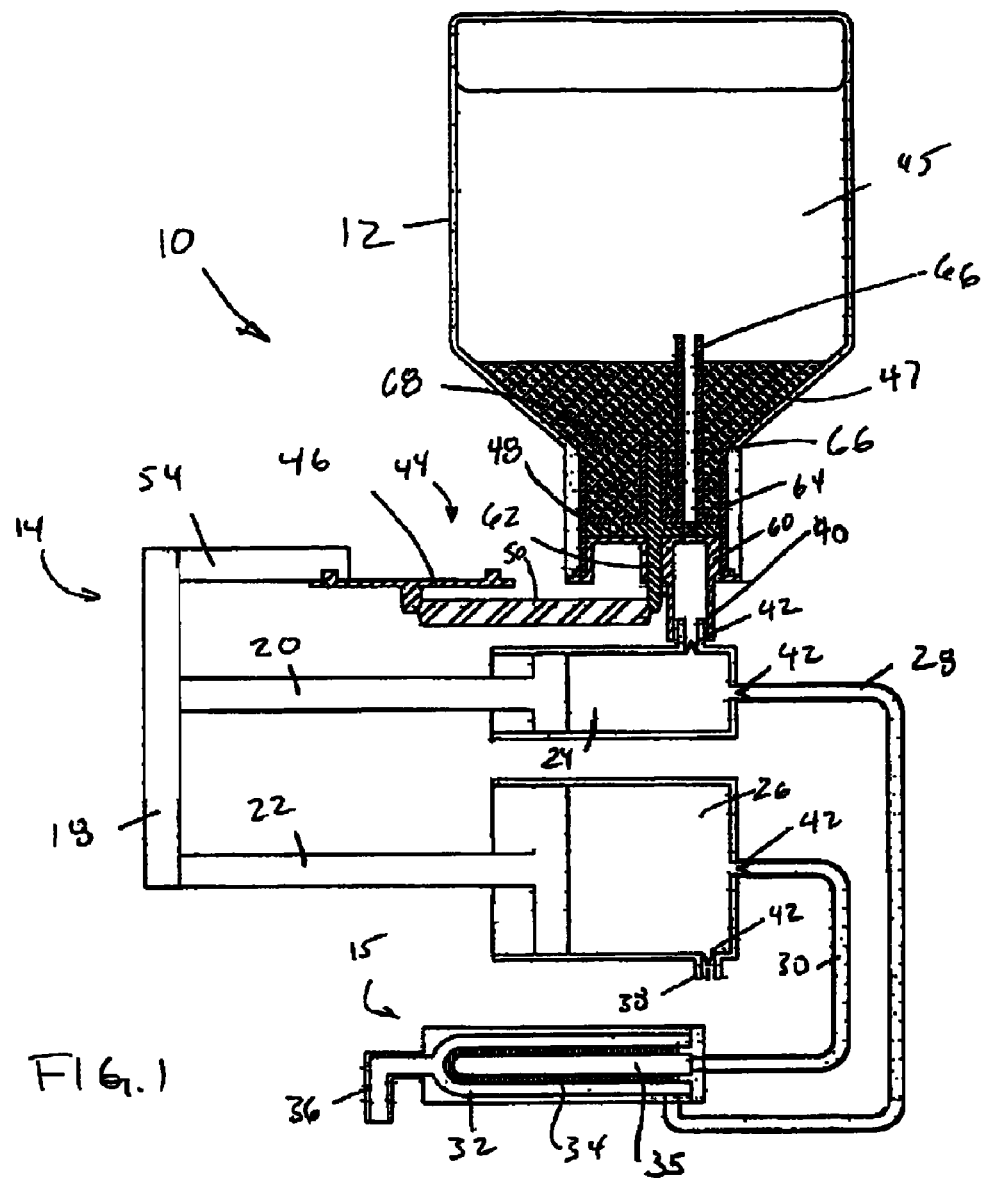
FIG. 1 is a cross sectional view of a first embodiment of a dispenser for dispensing foam with suspended particles constructed in accordance with the present invention.

Referring to FIG. 1 a first embodiment of a dispenser for dispensing foam with suspended particles is shown generally at 10. Dispenser 10 includes a collapsible liquid container 12, a pump mechanism 14 and a foaming component 15. This embodiment is for use in association with liquid that includes particles and wherein the particles will settle over time.

The pump mechanism 14 includes a drive bar 18 with a liquid piston 20 and an air piston 22. The liquid piston 20 moves in the liquid chamber 24 and the air piston 22 moves in the air chamber 26. The liquid chamber 24 and the air chamber 26 are connected by liquid conduit 28 and air conduit 30 respectively to the foaming component. Each chamber 24, 26 has an interior volume that is changeable responsive to the movement of the respective piston 20, 22. The relative sizes of the liquid chamber 24 and the air chamber 26 are arranged to provide the air to soap ratio desired for the resultant foam. This is described in more detail below.

The foaming component 15 includes a porous mandrel 34 and a mixing chamber 32. The interior of the porous mandrel 34 defines an air chamber 35. The porous mandrel is in the centre of the foaming component 15 and is generally a test tube shape. The mixing chamber 32 is an annular mixing chamber around the porous mandrel 34. The annular mixing chamber 32 generally follows the shape of the porous mandrel 34 and is generally an elongate annular tube. The porous mandrel 34 has an open end that is in flow communication with the air conduit 30. The mixing chamber has an exit nozzle or outlet 36.

The air chamber 26 has an air inlet 38. The liquid chamber 24 has a liquid chamber inlet 40. Non-retum valves 42 are positioned in the air inlet 38, the liquid inlet 40, the liquid conduit 28 and the air conduit 30. Preferably the non-retum valves 42 are positioned proximate to the liquid chamber 24 and the air chamber 26 respectively.

Figure 2:
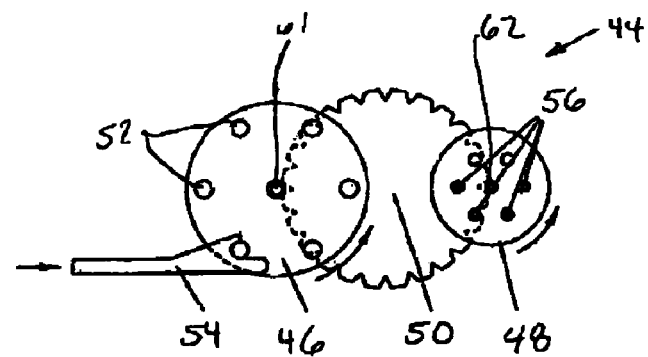
FIG. 2 is an enlarged plan view of the puck loading system of the dispenser for dispensing foam with suspended particles of FIG. 1.
Figure 3:
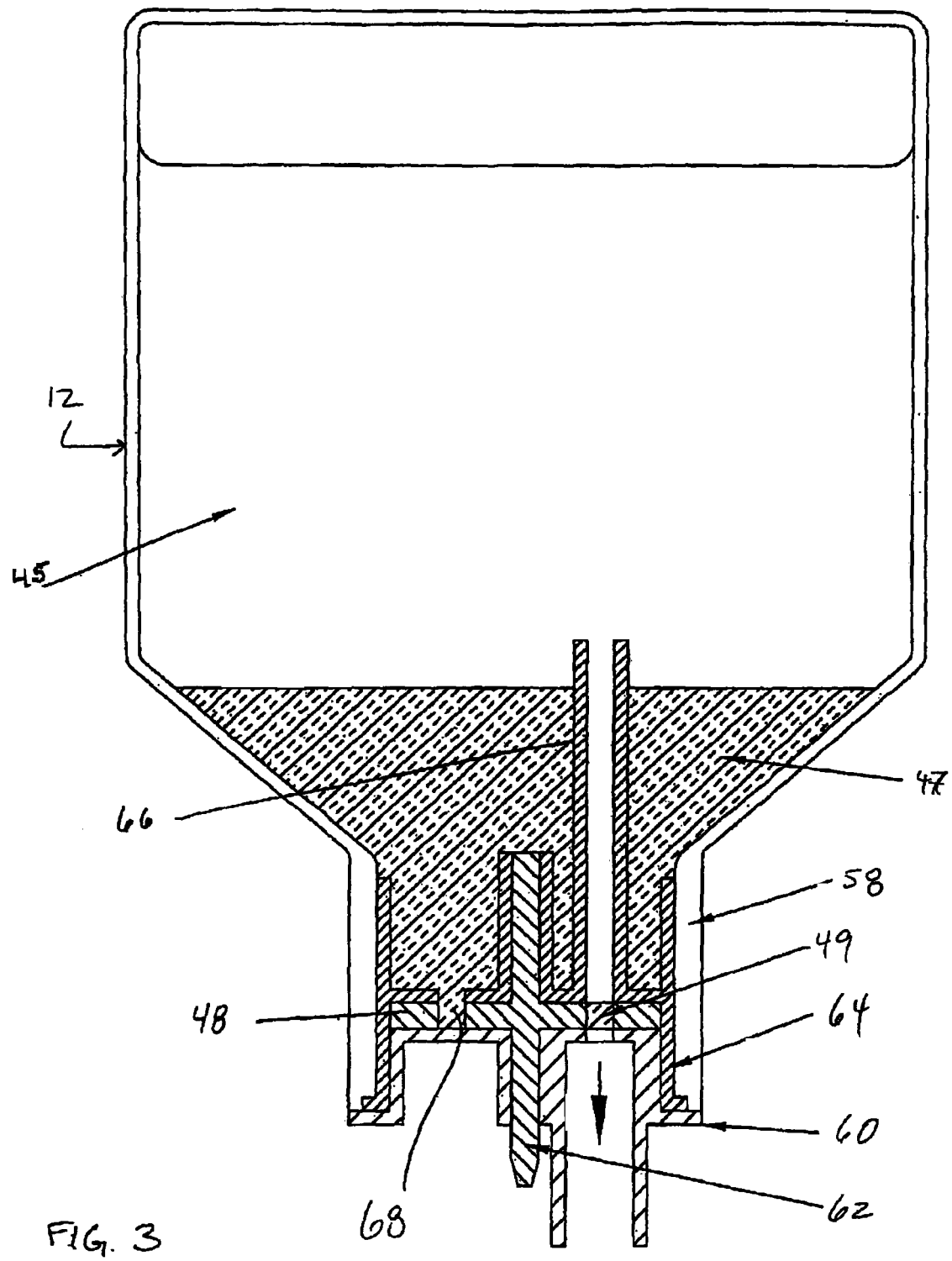
FIG. 3 is a cross sectional view of the container portion of the foam dispenser of FIG. 1.

Referring to FIGS. 1, 2 and 3, the container 12 is in flow communication with the liquid inlet 40 through the puck loading system 44. The puck loading system 44, as best seen in FIG. 2, incudes a drive wheel 46, a skim and load wheel 48 and an idler gear 50 therebetween. Idler gear 50 intermeshes with the central axis 61 of the drive wheel 46 and the central axis 62 of the skim and load wheel 48. The drive wheel 46 has a plurality of posts 52 extending upwardly therefrom. A drive wheel shaft 54 sequentially engages posts 52. Skim and load wheel 48 has a plurality of apertures 56 formed therein. Skim and load wheel 48 is rotatably positioned in throat 58 of container 12. A cap 60 holds skim and load wheel 48 in position. Skim and load wheel 48 has a central axis 62 that extends through cap 60 so that it engages idler gear 50. A feed insert 64 has a conduit 66 that extends upwardly into the container 12. Feed insert 64 has an aperture 68 formed therein which is sequentially in registration with aperture 56 in the skim and load wheel 48. Conduit 66 is similarly sequentially in registration with aperture 56 and when in registration it is in flow communication with liquid chamber inlet 40. Puck loading system 44 is designed to be used with liquid that has particles therein that sink. Thus the liquid is divided into a portion that has a low concentration of particles 45 and a high concentration of particles 47. A puck 49 (shown in FIG. 3) is a predetermined volume of liquid of high concentration particles.

In use, a person causes the drive bar 18 to move inwardly. This causes the liquid piston 20 and the air piston 22 to reduce the interior volume of the liquid chamber 24 and the air chamber 26 respectively. As well this causes the puck loading system to be activated. It will be appreciated by those skilled in the art that the drive bar 18 could be moved by simply pushing it forward but alternatively it could also be moved automatically responsive to a motion sensor or other type of sensor. The increase in pressure caused by moving pistons 20 and 22 will open non-return valves 42 in the liquid conduit 28 and air conduit 30 respectively. Air is pushed into the air chamber 35 of the foaming component 15 and liquid is pushed into the mixing chamber 32. The air in the air chamber 35 is pushed through the porous mandrel 34 forming bubbles in the liquid which results in a foam. The liquid in the container 12 includes particles which tend to sink. As stated above moving the drive bar 18 also causes the puck loading system to be activated. That is the drive wheel 46 engages a post 54 and moves it forwardly. This causes the drive wheel 46 to rotate which in turn causes the skim and load wheel 48 to rotate. When an aperture 56 in the ski and load wheel 48 is in registration with the aperture 68 in the feed insert 64 a puck is loaded. When that particular aperture is advanced such that it is in registration with conduit 66, that particular puck will drop down and when valve 42 in liquid inlet 40 is released the puck will be sucked into liquid chamber 24. When the drive bar 18 is released the drive bar moves back to the at rest position, causing a vacuum in the liquid chamber 24 and the air chamber 26 thus closing the valves 42 in the liquid conduit 28 and the air conduit 30 and opening the valves 42 in the liquid inlet 40 and the air inlet 38. Liquid and a puck then flow into the liquid chamber 24 and air flows into the air chamber 26. When equilibrium is reached the valves will close. The dispenser is then ready to dispense the next shot of foam.

Figure 4:
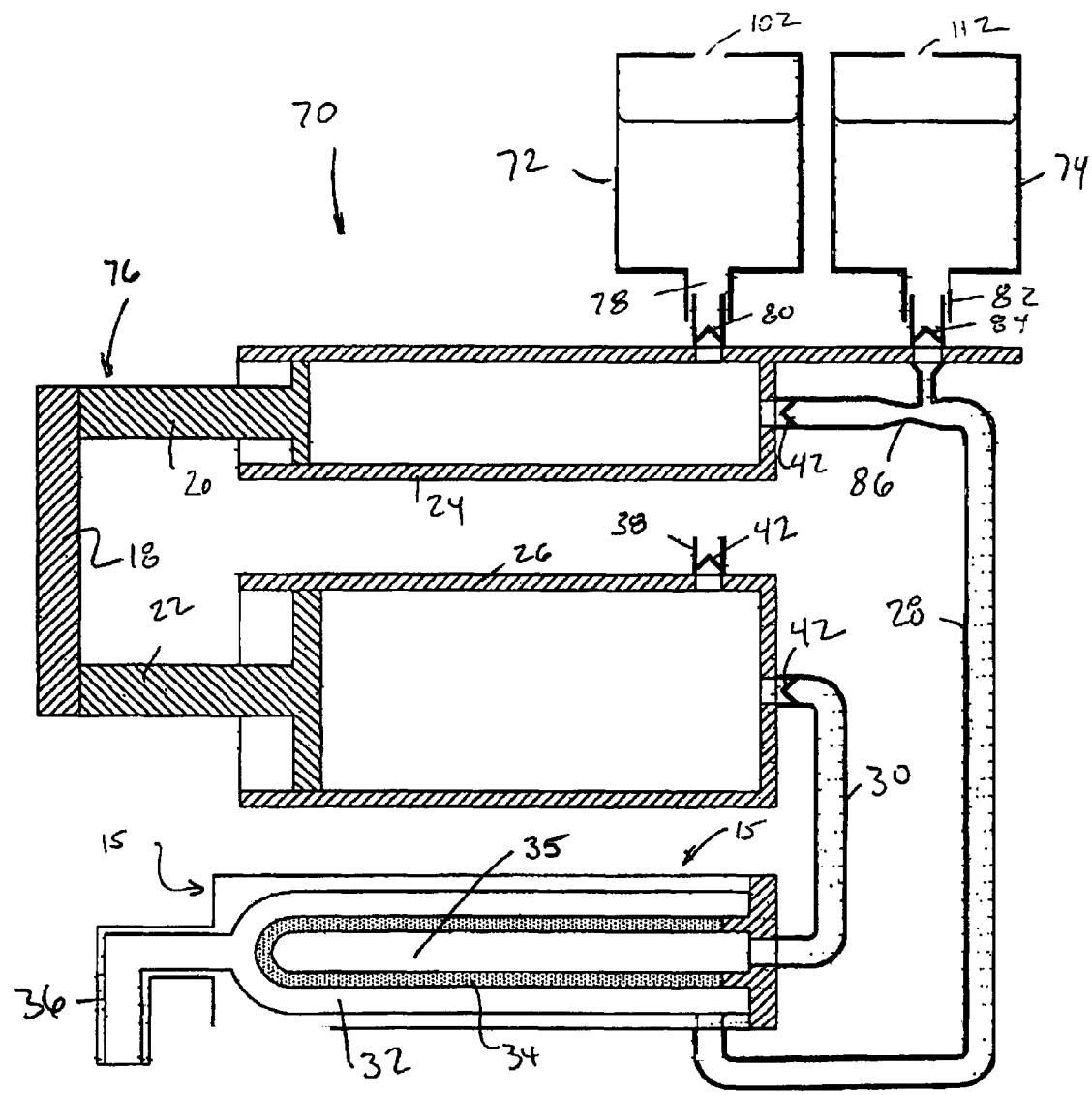
FIG. 4 is a cross sectional view of a second embodiment of a dispenser or dispensing foam with suspended particles of the present invention having two liquid supplies and an air piston and a liquid piston.

A second alternate embodiment of the dispenser for dispensing foam with suspended particles is shown generally at 70 in FIG. 4. In this embodiment there are first and second rigid liquid containers 72 and 74 respectively. The first liquid container 72 is a rigid container and is provided with an air hole 102. Similarly second liquid container 74 is a rigid container and is provided with an air hole 112. In this second alternate embodiment the containers are rigid containers but it will be appreciated by those skilled in the art that alternatively collapsible containers could be used. Most of the features of this embodiment are similar to those described above in regard to the first embodiment 10 and only those features that are different will be specifically discussed. This embodiment combines the liquid from the first liquid container 72 with the liquid from second liquid container 74. Typically one of the liquids will have a high concentration of particles and the other of the liquids will be generally particle-free. Foam dispenser 70 has a pump mechanism 76 similar to that described above, including a drive bar 18, a liquid piston 20 and an air piston 22. First liquid container 72 has an inlet 78 which is in flow communication with the liquid chamber 24. A non return valve 80 is positioned in inlet 78. Second liquid container 74 is in flow communication with liquid conduit 28 through inlet 82. A non return valve 84 is positioned in inlet 82. A venturi 86 is formed in liquid conduit 28 before inlet 82 and proximate thereto. Venturi 86 aids in the mixing of the liquid from the first container 72 with the liquid from the second container 74. Specifically, the venturi 86 is a restriction of flow that creates a vacuum on its right side, and sucks liquid from second container 74 into the system to fill the void. The liquid with a high concentration of particles may be positioned in either first container 72 or second container 74 but preferably it will be positioned in second container 74. The remainder of dispenser 70 is as described above in regard to dispenser 10.

In use, the second embodiment of the dispenser 70 functions very similarly to the first embodiment. The main difference between these two embodiments is that the second embodiment has first and second liquid containers 72, 74 which are in flow communication with the liquid conduit 28.

To initiate foaming the drive bar 18 is moved inwardly, thus moving pistons 20 and 22 into their respective chambers 24, 26. The increase in pressure caused by moving pistons 20 and 22 will open non-return valves 42 in the liquid conduit 28 and air conduit 30 respectively. Venturi 86 aids in the mixing of liquid from liquid containers 72 and 74. When the liquid from the first and second containers are mixed the resulting combination, in a preferred embodiment, has a viscosity of about 100 centipose. The resulting combination will be mechanically unstable in that the particles will tend to either float or sink depending on the particular particles used. As discussed above preferably second liquid container 74 will have a higher concentration of particles suspended therein. Air is pushed into the air chamber 35 of the foaming component 15 and liquid is pushed into the mixing chamber 32. The air in the air chamber 35 is pushed through the porous mandrel 34 forming bubbles in the liquid which results in a foam. When the drive bar 18 is released the drive bar moves back to the at rest position, causing a vacuum in the liquid chamber 24 and the air chamber 26 thus closing the valves 42 in the liquid conduit 28 and the air conduit 30 and opening the valves 80, 84 in the liquid inlets 78, 82 and valve 42 in the air inlet 38. Liquid flows into the liquid chamber 24 and liquid conduit 28 and air flows into the air chamber 26. When equilibrium is reached the valves will close. The dispenser is then ready to dispense the next shot of foam.

Figure 5:
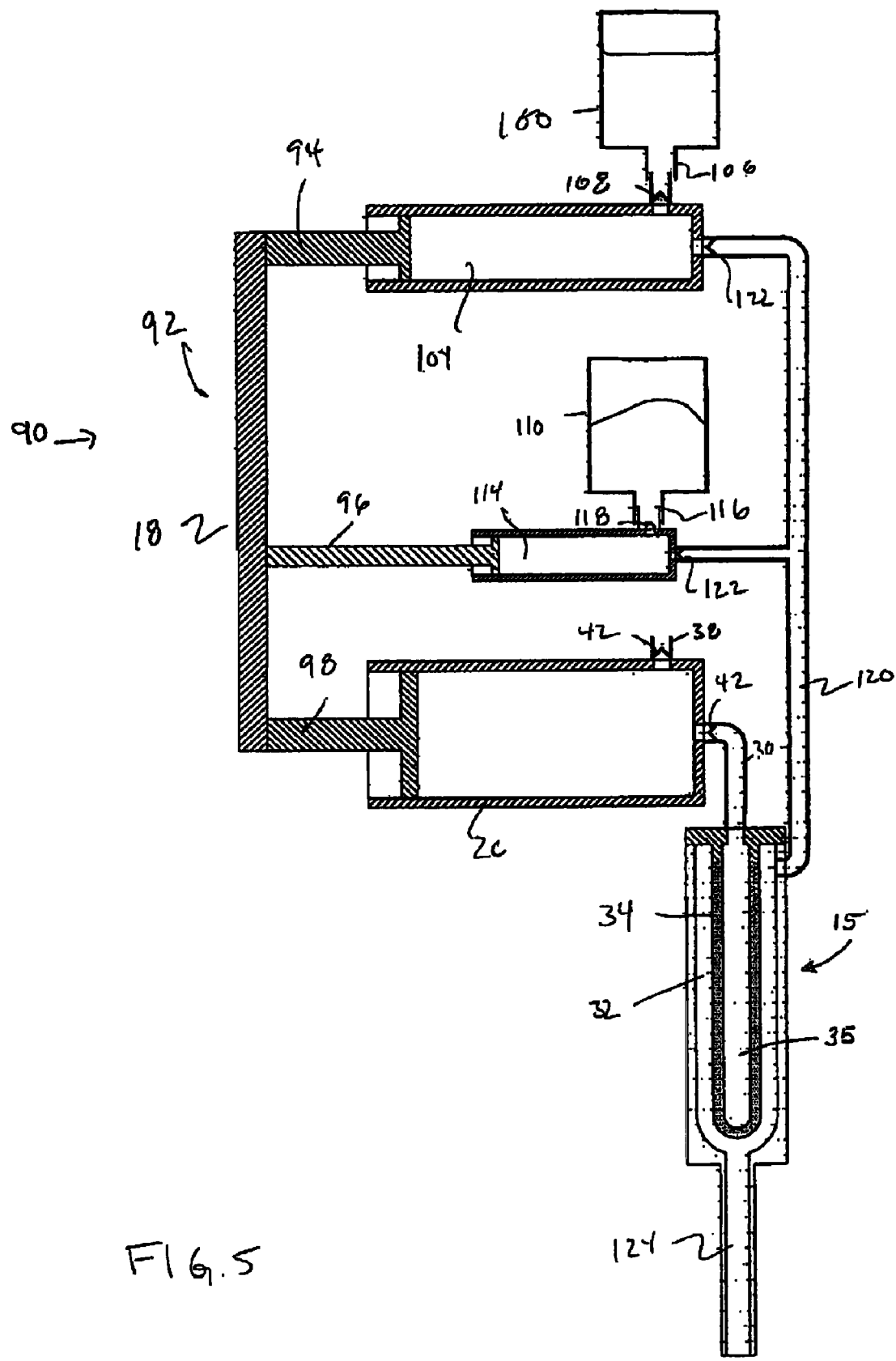
FIG. 5 is a cross sectional view of a third embodiment of a dispenser for dispensing foam with suspended particles of the present invention having two liquid supplies, a piston for each liquid supply and an air piston.

The third alternate embodiment of the dispenser for dispensing foam with suspended particles is shown generally at 90 in FIG. 5. In this embodiment there are a first and a second collapsible container, 100 and 110 respectively. This third embodiment is similar to those shown above but a separate piston is provided for the second liquid container 110. Specifically, the pump mechanism 92 includes first liquid piston 94, a second liquid piston 96 and an air piston 98, all of which are driven by drive bar 18. First liquid container 100 is in flow communication with a first liquid chamber 104 through inlet 106. A non-return valve 108 is positioned therein. Second liquid container 110 is in flow communication with a second liquid chamber 114 through inlet 116. A non-return valve 118 is positioned therein.

Generally the second liquid container 110 will have a liquid with a high particle concentration and the first liquid container 100 has generally no particles. The high particles liquid and the no particles liquid are combined in conduit 120. Conduit 120 is in flow communication with first liquid chamber 104 and second liquid chamber 114 through non return valves 122.

As in the previous embodiments there is a foaming component 15. The air conduit 30 is in flow communication with the mixing chamber 32 through the porous mandrel 34. Similarly the liquid is in flow communication with the mixing chamber 32.

In this embodiment the mandrel 34 and mixing chamber 32 are oriented vertically. In this embodiment the mixing chamber is provided with an elongate exit nozzle 124.

In use, the third embodiment of the dispenser 90 functions very similarly to the second embodiment. The main difference between these two embodiments is that the third embodiment has a separate piston for each liquid container 100 and 110. To initiate foaming the drive bar 18 is moved inwardly, thus moving pistons 94, 96 and 98 into their respective chambers 104, 114, and 26. The increase in pressure caused by moving liquid pistons 94, 96 and air piston 98 will open non-return valves 122, 42 in the liquid conduit 120 and air conduit 30 respectively. Air is pushed into the air chamber 35 of the foaming component 15 and liquid is pushed into the mixing chamber 32. The air in the air chamber 35 is pushed through the porous mandrel 34 forming bubbles in the liquid which results in a foam. When the drive bar 18 is released the drive bar moves back to the at rest position, causing a vacuum in the liquid chambers 104,114 and the air chamber 26 thus closing the valves 122, 42 in the liquid conduit 120 and the air conduit 30, respectively and opening the valves 108, 118 in the liquid inlets 106, 116 and valve 42 in the air inlet 38. Liquid flows into the liquid chamber 104 and 114 and liquid conduit 120 and air flows into the air chamber 26. When equilibrium is reached the valves will close. The dispenser is then ready to dispense the next shot of foam.

Figure 6:
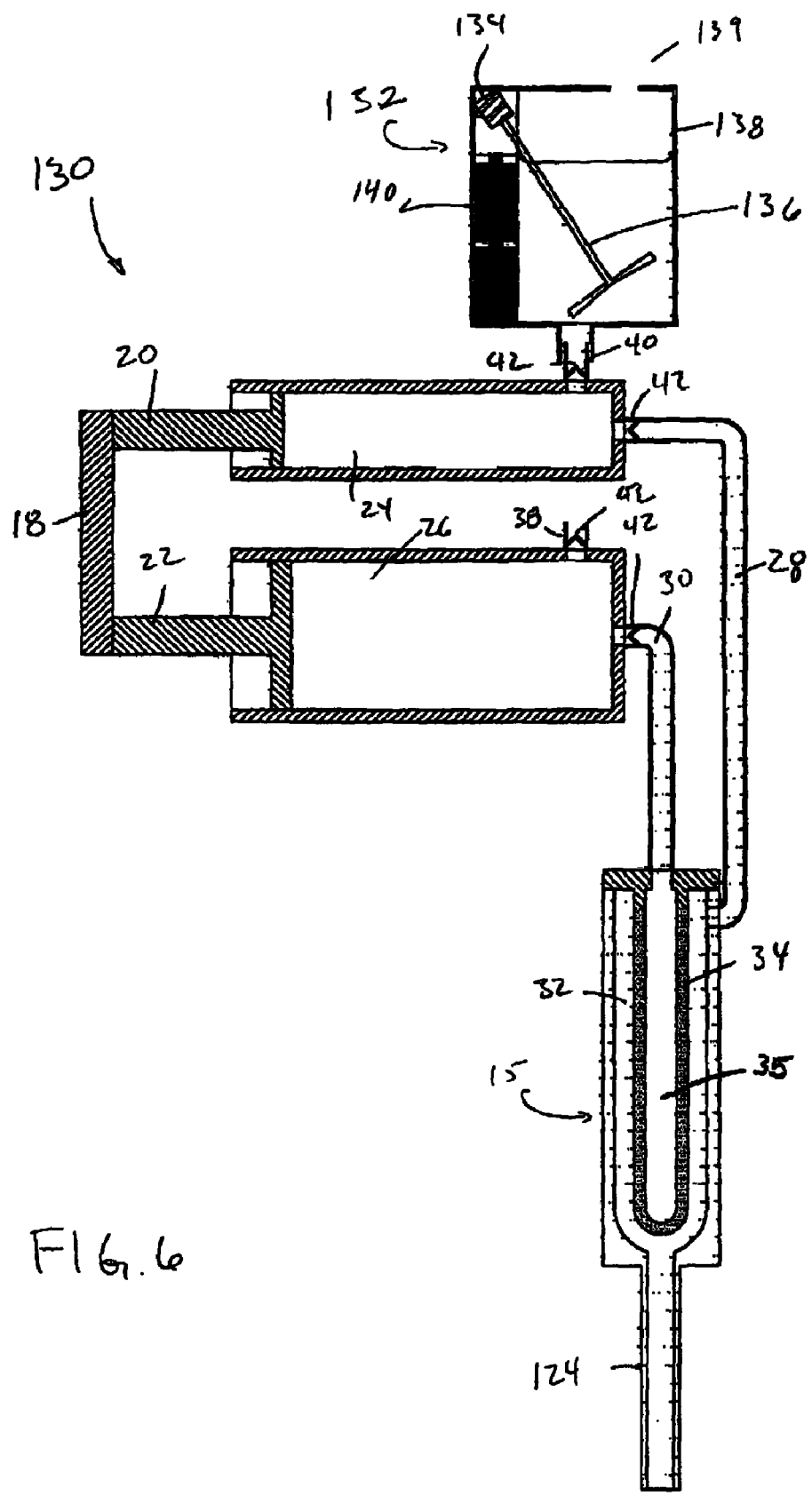
FIG. 6 is a cross sectional view of a fourth embodiment of a dispenser for dispensing foam with suspended particles of the present invention having an agitation device in the liquid container.

The fourth embodiment of the dispenser for dispensing foam with suspended particles is shown generally at 130 in FIG. 6. The fourth embodiment includes an agitator mechanism 132. The fourth embodiment has some features similar to those found in the first embodiment and the third embodiments. Specifically the fourth embodiment includes a liquid piston 20 and an air piston 22 operably connected to a drive bar 18. The liquid chamber 24 is in flow communication with the mixing chamber 32 of the foaming component 15 via the liquid conduit 28. The air chamber 26 is in flow communication via the air conduit 30 with the mixing chamber 32 through the porous mandrel 34. As in the third embodiment the mixing chamber 32 and the porous mandrel 34 are oriented vertically and the mixing chamber 32 has an elongate exit nozzle 124.

The agitator mechanism 132 includes a motor 134 and an agitator device 136. The agitator device. 136 extends into the interior of the liquid container 138. The liquid container 138 is a rigid container and is provided with a vent hole 139. Preferably the agitator device is a pin wheel but it will be appreciated by those skilled in the art that a number of alternate agitator devices could also be used. Preferably the motor 134 is an electric motor and it is powered by batteries 140.

In use the fourth embodiment 130 functions similarly to those described above. The main difference is that when drive bar 18 is moved forwardly the agitator mechanism is activated. Specifically when activated the pin wheel will rotate thus mixing the particles that have either sunk to the bottom or floated to the top and thus when the liquid is sucked into the liquid chamber 24 a mixture of liquid and particles is sucked into the liquid chamber 24.

Figure 7:
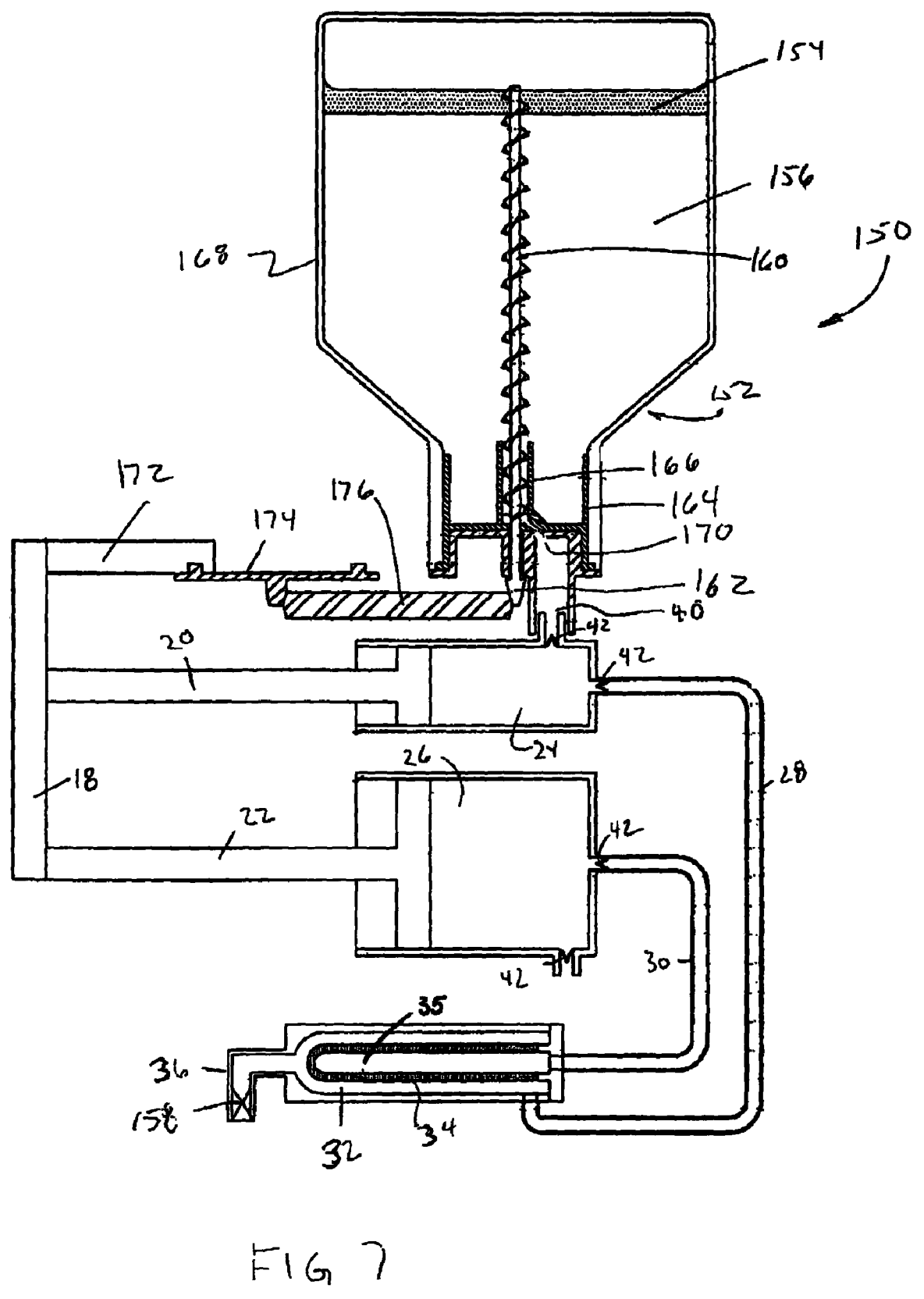

The fifth embodiment of the dispenser for dispensing foam with suspended particles is shown generally at 150 in FIG. 7. The fifth embodiment is similar to that shown in FIG. 1 but It includes a skimming mechanism 152. This embodiment is adapted for use in association with liquid that has particles 154 which over time will float to the top of the liquid 156. The skimmer mechanism is adapted to skim the floating particles from the top. Specifically, the fifth embodiment includes a liquid piston 20 and an air piston 22 operably connected to a drive bar 18. A liquid chamber 24 is in flow communication with the mixing chamber 32 of the foaming component 15 via the liquid conduit 28. Similarly, the air chamber 26 is in flow communication via the air conduit 30 with the mixing chamber 32 through the porous mandrel 34. As in the first embodiment the mixing chamber 32 and the porous mandrel 34 are oriented horizontally. An exit nozzle or mixing chamber outlet 36 has an elastomeric valve 158 positioned therein.

The skimming mechanism 152 includes a scooped auger 160 connected to an auger wheel 162. A cap 164 is provided with an auger sleeve 166 extending upwardly into the interior of container 168. The top of the sleeve 166 is open to the liquid 156 in the interior of the container 168. Thus as the scooped auger 160 turns it scoops particles 154 that have floated to the top. The auger 160 moves particles 154 to the top of the container. At the same time liquid 156 flows into the sleeve 166. The sleeve has an outlet 170 that is in flow communication with liquid chamber inlet 40. The auger wheel 162 is operably connected to the drive bar 18 using a drive wheel shaft 172, a drive wheel 174 and an idler gear 176. These are connected in a similar fashion as drive wheel 46 and skim and load wheel 48 shown in FIG. 2.

In use the fifth embodiment 150 functions similarly to the first embodiment. When the drive bar is moved forwardly the skimming mechanism 152 is activated. Specifically the scooped auger 160 is rotated. As the scooped auger rotates it scoops up particles 154 that have floated to the top and carries them down to the sleeve 166 and outlet 170. Thus when valve 42 in liquid inlet 40 is opened a mixture of liquid and particles enters liquid chamber 24.

Figure 8:
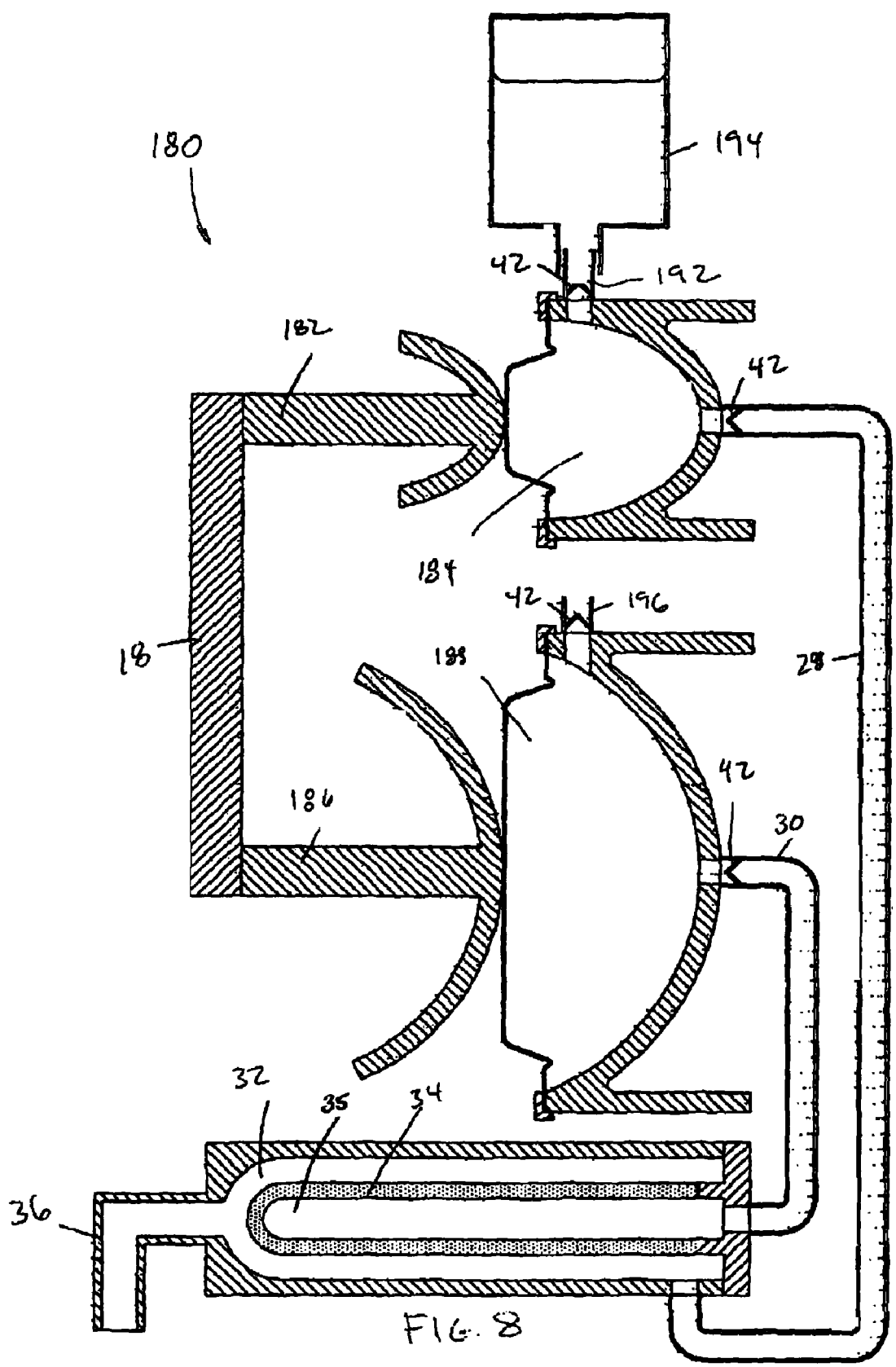
FIG. 8 is a cross sectional view of a sixth embodiment of a dispenser for dispensing foam with suspended particles of the present invention having a liquid diaphragm pump and an air diaphragm pump.

The sixth embodiment of the dispenser for dispensing foam with suspended particles is shown generally at 180 in FIG. 8. This is similar to that shown in FIG. 1 but using diaphragm type pistons. This embodiment is adapted to be used with a single homogeneous liquid. However, it will be appreciated by those skilled in the art that this embodiment can easily be modified to include a skimmer, an agitator or a puck loading system.

The sixth embodiment 180 includes a liquid diaphragm piston 182, a liquid chamber 184, an air diaphragm piston 186 and an air chamber 188. The liquid diaphragm piston 182 and the air diaphragm piston 186 are operably connected to a drive bar 18. As in the above embodiments a liquid conduit 28 is in flow communication with the liquid chamber 184 and an air conduit 30 is in flow communication with the air chamber 188. The liquid chamber 184 has an inlet 192 in flow communication with the collapsible liquid container 194. The air chamber 188 has an air inlet 196. Non-retum valves 42 are positioned in the liquid chamber inlet 192, the liquid conduit 28, the air inlet 196 and the air conduit 30. The air conduit 30 is in flow communication with the mixing chamber 32 through the porous mandrel 34. The liquid conduit 28 is in flow communication with the mixing chamber 32 of the foaming component. A mixing chamber exit nozzle 36 extends from the mixing chamber 32.

In use the sixth embodiment 180 functions similar to those described above but rather than piston pumps it uses diaphragm pumps. In addition it has a single liquid container input.

The seventh embodiment of the dispenser for dispensing foam with suspended particles of the present invention is shown generally at 200 in FIG. 9. The seventh embodiment combines many of the features shown in the previous embodiments. Specifically, the seventh embodiment uses a rigid container 202 having a vent hole 204 formed in the top thereof. As discussed above the liquid may be foamable liquid with or without particles suspended therein. The remainder of dispenser 200 is similar to that shown in FIG. 6. Specifically the seventh embodiment includes a liquid piston 20 and an air piston 22 operably connected to a drive bar 18. A liquid chamber 24 is in flow communication with the mixing chamber 32 of the foaming component 15 via the liquid conduit 28. Similarly, the air chamber 26 is in flow communication, via the air conduit 30, with the mixing chamber 32 through the porous mandrel 34. The mixing chamber 32 and the porous mandrel 34 are oriented vertically and it has an elongate exit nozzle 124.

In use the seventh embodiment 200 functions similar to those described above but as with the sixth embodiment it has a single liquid container input.

Figure 10:
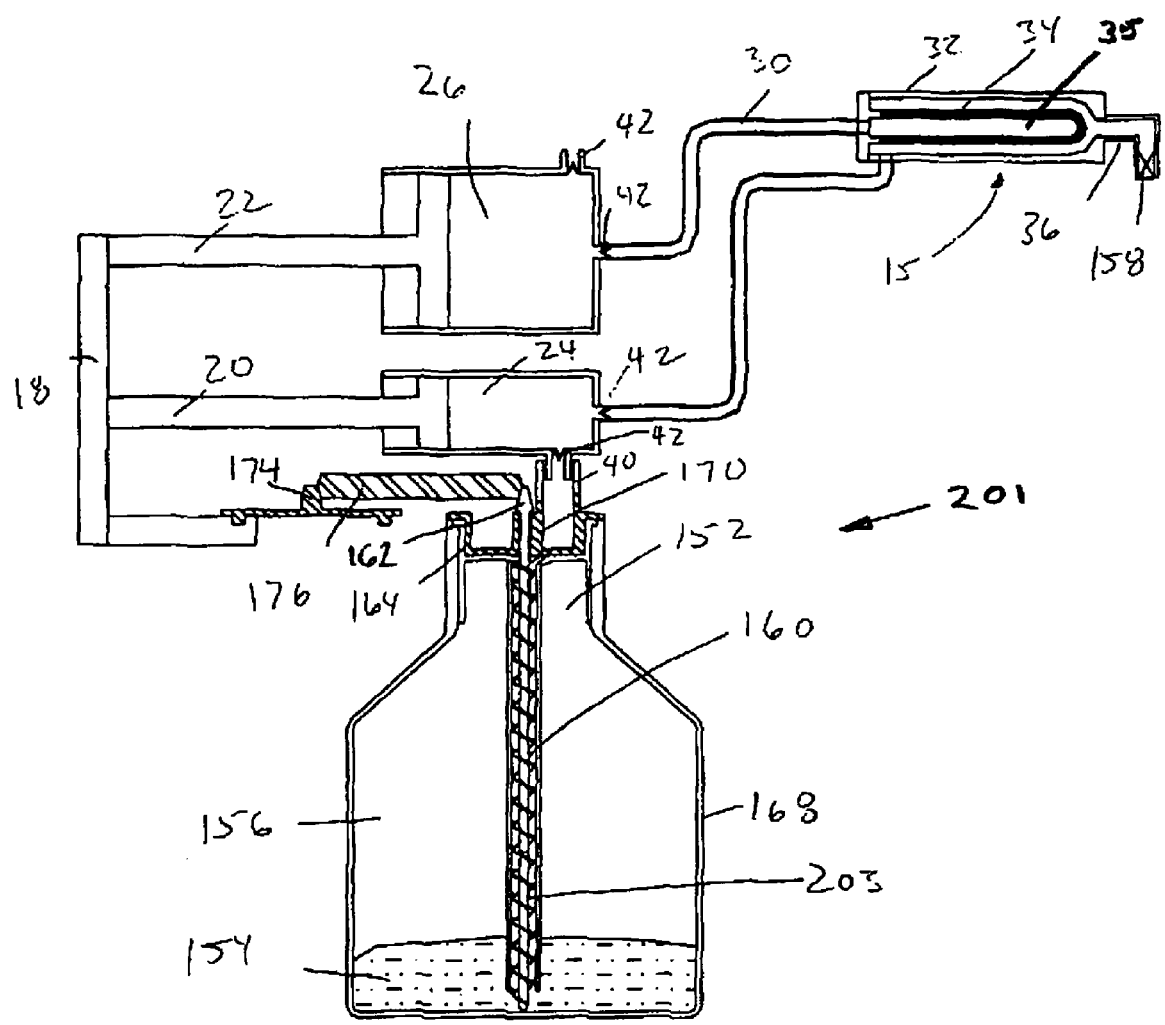
FIG. 10 is a cross sectional view of an eighth embodiment of the dispenser for dispensing foam with suspended particles of the present invention having an upright liquid container with an auger mechanism.

The eighth embodiment of the dispenser for dispensing foam with suspended particles is shown generally at 201 in FIG. 10. The eighth embodiment is similar to that shown in FIG. 7 but the liquid container 168 is positioned upright. This embodiment is adapted for use in association with liquid that has particles 154 which over time sink to the bottom of the liquid 156. The auger mechanism is essentially the same as the skimmer mechanism described above and it is adapted to move particles that have sunk to the bottom. Specifically, the eighth embodiment includes a liquid piston 20 and an air piston 22 operably connected to a drive bar 18. A liquid chamber 24 is in flow communication with the mixing chamber 32 of the foaming component 15 via the liquid conduit 28. Similarly, the air chamber 26 is in flow communication via the air conduit 30 with the mixing chamber 32 through the porous mandrel 34. As in the first embodiment the mixing chamber 32 and the porous mandrel 34 are oriented horizontally. An exit nozzle or mixing chamber outlet 36 has an elastomeric valve 158 positioned therein.

The auger or skimming mechanism 152 includes a scooped auger 160 connected to an auger wheel 162. A cap 164 is provided with an auger sleeve 203 extending upwardly into the interior of container 168. In this embodiment the auger sleeve 203 extends to proximate to the bottom of container 168. Thus as the scooped auger 160 turns it scoops particles 154 that have sunk to the bottom. The auger 160 moves particles 154 to the bottom of the container. At the same time liquid 156 flows into the sleeve 203. The sleeve has an outlet 170 that is in flow communication with liquid chamber inlet 40. The auger wheel 162 is operably connected to the drive bar 18 using a drive wheel shaft 172, a drive wheel 174 and an idler gear 176. These are connected in a similar fashion as drive wheel 46 and skim and load wheel 48.

In use the eighth embodiment 201 operates the same as the fifth embodiment 150 but the auger moves particles from the bottom of the container 168 to the top of the container.

Figure 11:
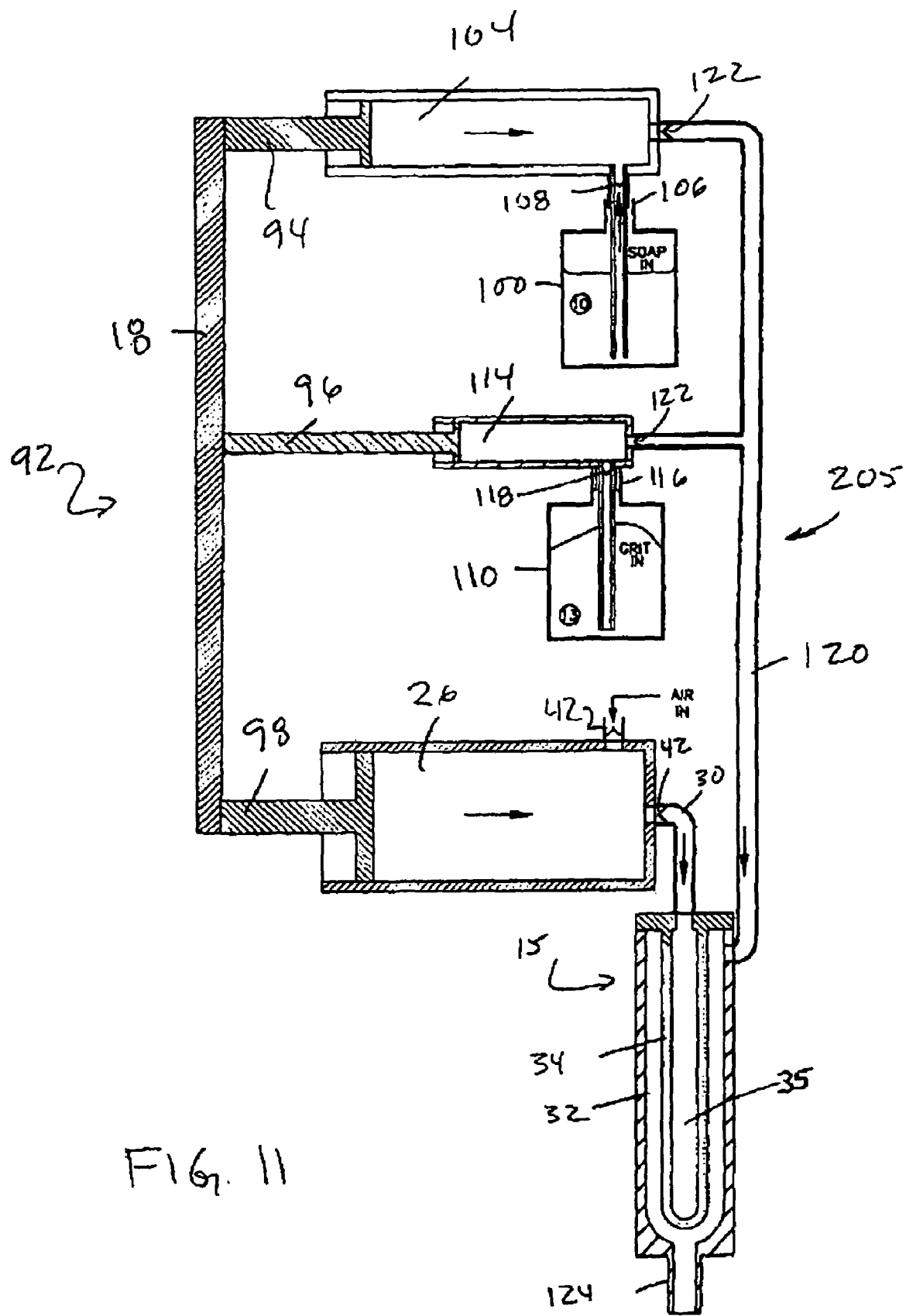
FIG. 11 is a cross sectional view of a ninth embodiment of the dispenser for dispensing foam with suspended particles of the present invention having two upright liquid containers.

FIG. 11 shows a ninth embodiment 205 which is essentially the same as the embodiment shown in third embodiment 90 in FIG. 5. Specifically, the pump mechanism 92 includes first liquid piston 94, a second liquid piston 96 and an air piston 98, all of which are driven by drive bar 18. First liquid container 100 is in flow communication with a first liquid chamber 104 through inlet 106. A non-retum valve 108 is positioned therein. Second liquid container 110 is in flow communication with a second liquid chamber 114 through inlet 116. A non-return valve 118 is positioned therein.

Generally the second liquid container 110 will have a liquid with a high particles concentration and the first liquid container 100 has generally no particles. The high particles liquid and the no particles liquid are combined in conduit 120. Conduit 120 is in flow communication with first liquid chamber 104 and second liquid chamber 114 through non return valves 122.

As in the previous embodiments there is a foaming component 15. The air conduit 30 is in flow communication with the mixing chamber 32 through the porous mandrel 34. Similarly, the liquid is in flow communication with the mixing chamber 32. in this embodiment the mandrel 34 and mixing chamber 32 are oriented vertically. In this embodiment the mixing chamber is provided with an elongate exit nozzle 124.

It will be appreciated by those skilled in the art that the embodiments with the upright containers are shown by way of example only and that embodiments with the inverted containers may be adapted to be used with upright containers. Further it will be appreciated by those skilled in the art that the upright containers are particularly useful as under the counter soap dispensers.

FIG. 12 shows a second embodiment of the foaming component 209. The foaming component 209 includes a mixing chamber 210 and a porous mandrel 34. Mixing chamber 210 is generally annular and has an upstream wide annular portion 212 and downstream narrow annular portion 214. A smooth transition is 216 is provided between the upstream annular portion 212 and the downstream annular portion 214. It will be appreciated by those skilled in the art that the foaming component 209 may be oriented either horizontally or vertically.

Figure 13:
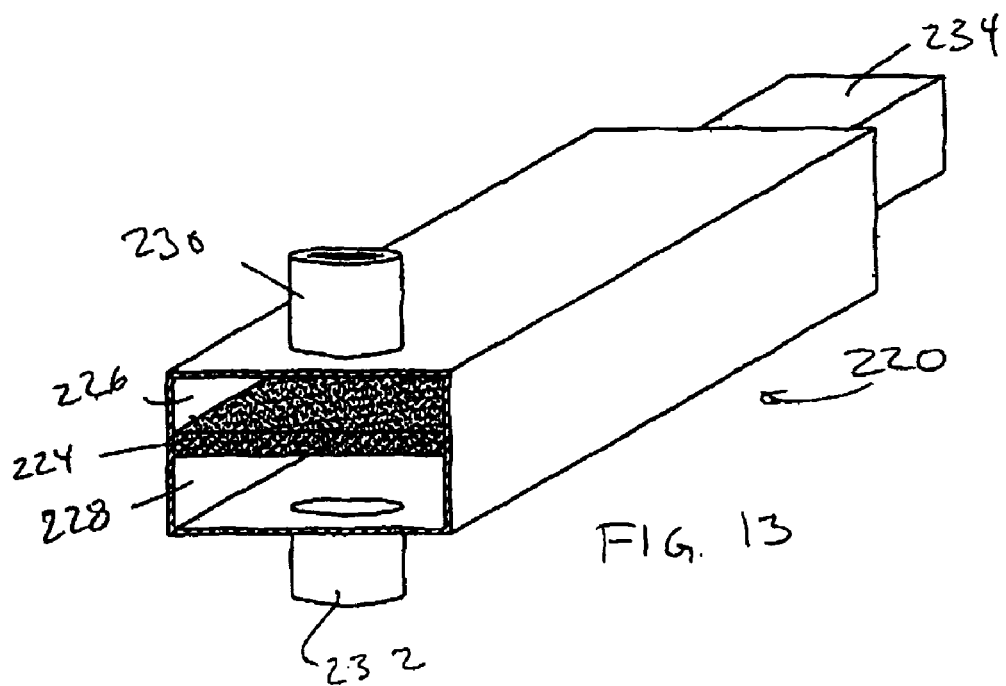
FIG. 13 is a partial perspective view of a third alternate foaming component of a dispenser for dispensing foam with suspended particles wherein the mixing chamber uses a cross flow arrangement with a porous material therebetween.
Figure 14:
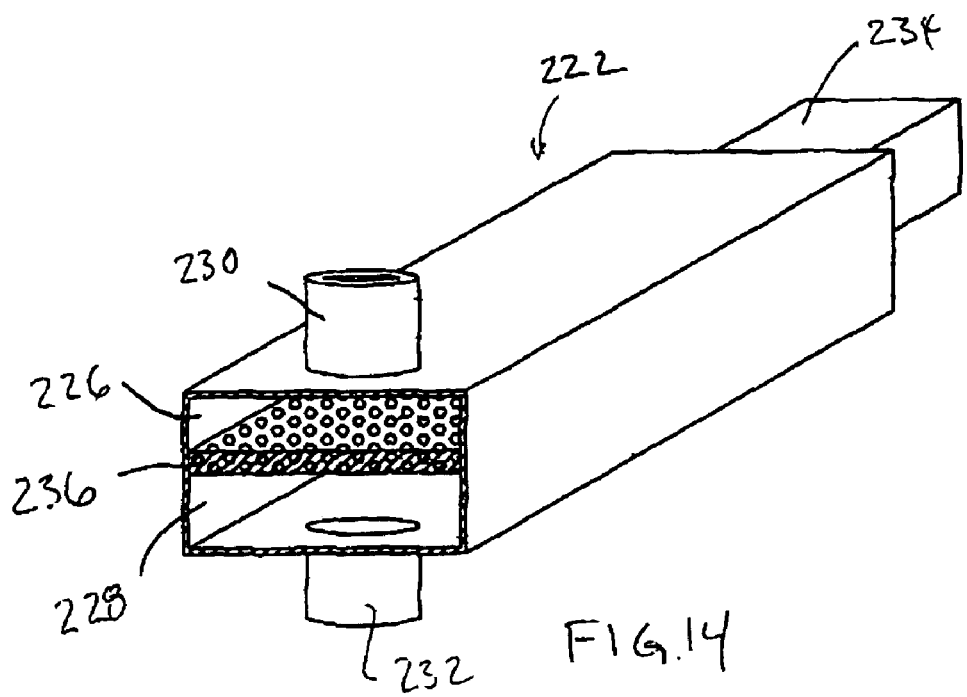
FIG. 14 is a partial perspective view of a fourth alternate foaming component of a dispenser for dispensing foam with suspended particles wherein the mixing chamber uses a cross flow arrangement with a solid material therebetween the material has a plurality of small holes.

Third and fourth embodiments of foaming component are shown generally at 220 and 222 respectively in FIGS. 13 and 14. It will be appreciated by those skilled in the art that the foaming components shown in the previous embodiments are a preferred configuration of the foaming components. The previous foaming components 15 include a mixing chamber 32 that is generally an annular elongate chamber positioned around a porous mandrel 34. Alternatively the foaming component includes a mixing chamber that is a stepped annular mixing chamber. The porous mandrel 34 in those embodiments acts as an air sparging element. Generally the objective is to maximize the air that is bubbled into the liquid. In order to achieve this an interface or air sparging element is provided between the air and the liquid through which liquid passes. A porous material provides a plurality of microscopic holes through which the air may pass. Alternatively a mesh or grid could be provided through which the air must pass. As discussed above the preferred embodiment includes a porous mandrel 34 and an annular mixing chamber 32. This provides a good use of space in conjunction with a reasonable surface area through which the air must pass. However it will be appreciated by those skilled in the art that there are a number of configurations which would also work.

Examples of two alternate foaming components are shown in FIGS. 13 and 14. Foaming component 220 is a generally elongate rectangular box with an air sparging plate 224 therein. The air sparging plate 224 divides the foaming component 220 into an air chamber 226 and a mixing chamber 228. An air inlet 230 directs air from the pump mechanism into the air chamber portion of the foaming component 220.

Similarly a liquid inlet 232 directs liquid from the pump mechanism into the mixing chamber 228. The mixing chamber 228 is provided with an outlet 234. The liquid is typically soap or a soap particles mixture. As in previous embodiments air is pushed into the foaming component and pushed through the air sparging plate or mandrel to create air bubbles in the liquid. The air sparging plate 224 shown in FIG. 13 is made of a porous material. Alternatively the air sparging plate could be made of a solid material with a plurality of holes as shown at 236 in FIG. 14. The remaining features of the foaming component 222 shown in FIG. 14 are the same as those shown in FIG. 13. It will be appreciated by those skilled in the art that there are a number of materials that may be used as an air sparging element. Some examples are sintered polyethylene, sintered bronze, sintered stainless steel, micro porous materials PTFE PolyTetraFlourEthylene (eg GORTEX™), micro porous urethane (eg Porelle®) micro porous ceramics, non woven polyester and acrylic mats or multi-layer stainless steel gauze, to name a few.

Figure 15:
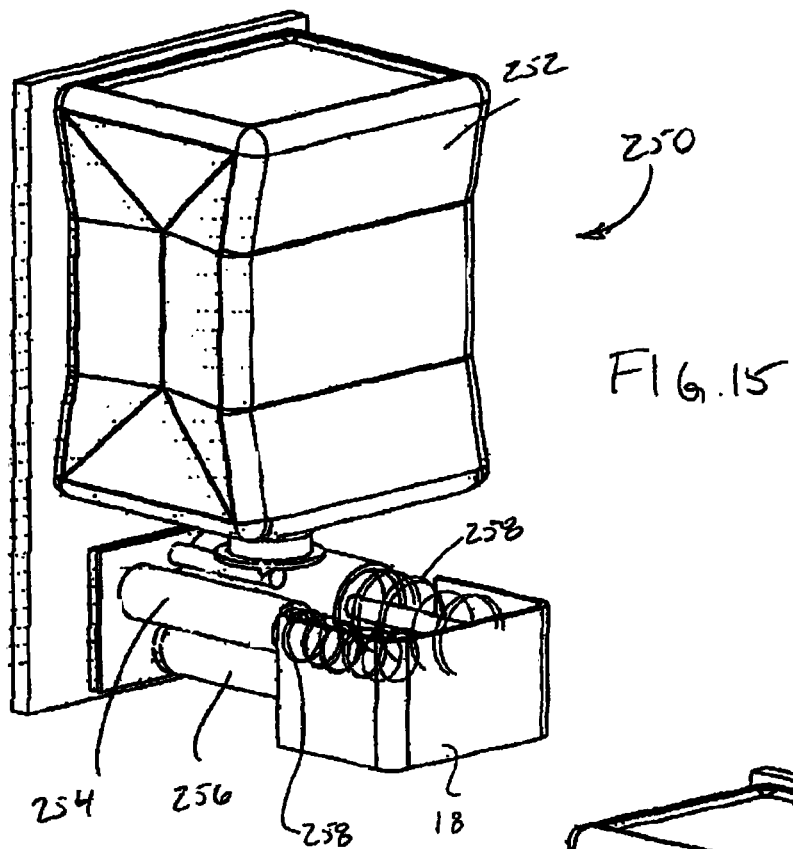
FIG. 15 is a perspective view of a tenth embodiment similar to the seventh embodiment but with a collapsible container and looking from the left side.
Figure 16:
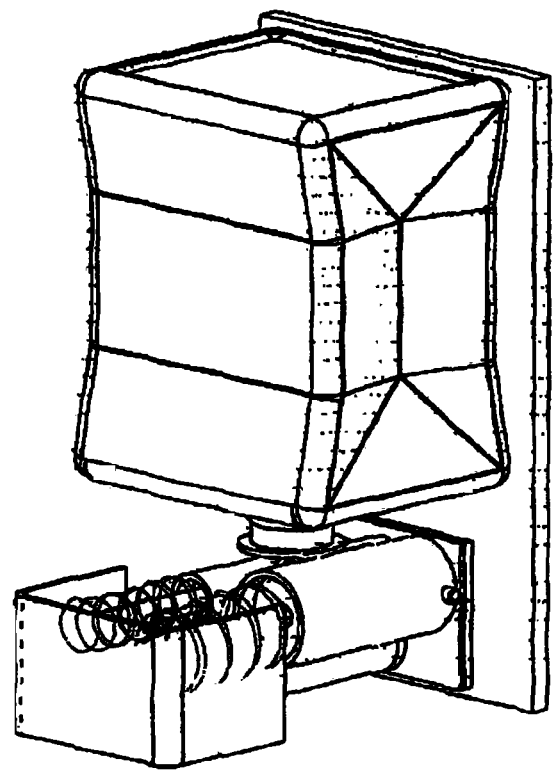
FIG. 16 is a perspective view of the tenth embodiment similar to FIG. 15 but looking from the right side.

It will be appreciated by those skilled in the art that FIGS. 1-14 are chematic representations of the invention herein. Specifically, the containers shown in hese figures are generally not to scale. It will be appreciated that the containers could come in a variety of sizes. A tenth embodiment of the dispenser for dispensing foam with suspended particles of the present invention is shown generally at 250 in FIGS. 15 and 16. These figures show one configuration of the relative sizes of the collapsible container 252, the pump mechanism 254 and the foaming component 256. This embodiment is similar to the seventh embodiment 200 shown in FIG. 9 but with a collapsible container. The dispenser would likely also include a protective cover (not shown) to ensure that non-authorized people cannot access the mechanisms. In all of the embodiments there is a biasing means such as springs 258 to move the drive bar 18 into the at rest or fully extended position. This configuration could easily be adapted to accommodate a rigid container, two containers, a vertical foaming component or any of the other variations described above.

It will be appreciated by those skilled in the art that there are a number of parameters that may be varied in regard to the dimensions in the foaming component. For example, as discussed above, the material of the mandrel, the length of the mandrel, the width of the annular mixing chamber and the length of the mixing chamber outlet may be varied. In order to determine the dimensions that will be used a method of evaluating the foam was developed.

Figure 17:
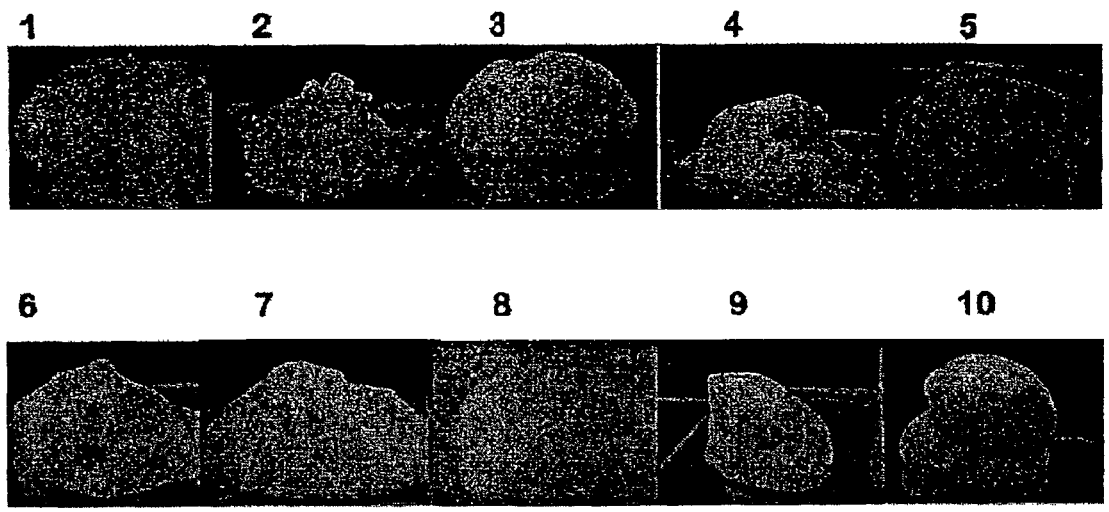
FIG. 17 is a series of photographs showing a scale of foam bubble sizes.
Figure 18:
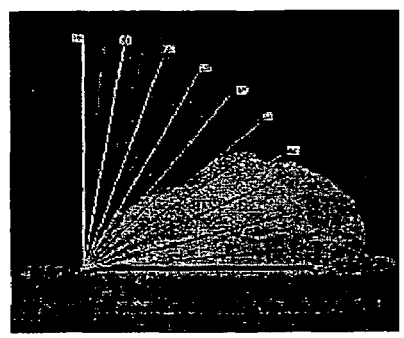
FIG. 18 is a photograph of the scale for the pride of foam.

The inventors developed a method of evaluating the foam to help in the design of the specific dimensions of the foaming component. The foam is evaluated in terms of the bubble size, the pride, the bubble stamina, coverage and rinse. The bubble size was determined by obtaining one shot of foam from the dispenser being analyzed. The size of the bubbles was determined using the scale shown in FIG. 17 as a guide. Decimal points were used to distinguish between bubbles that fell between two bubble sizes. Pride is used to describe the foam stiffness, specifically the ability of the foam to hold its shape and not sag down and spread out. To determine the pride a photograph of the foam shot was taken on a level with the foam. A protractor superimposed on the photographic image to measure the internal angle. An angle of 70 is very proud; closer to 10 degrees is shy. An example of this is shown in FIG. 18. The bubble stamina was determined by measuring the time that the bubbles last while rubbing hands together. The foam coverage was determined by first discharging three shots of foam onto a dish, weighing the dish with the foam, removing foam from the dish until the users hands are well covered and determining the amount used and thus the foam coverage. The ability of the foam to be rinsed off is also an important characteristic. To determine the ability to rinse the foam, a test was performed wherein a funnel was attached to a faucet to ensure a constant flow rate and the user's hands were covered with foam and thereafter were rinsed while catching the water in a large measuring cup or bowl and then weighing the water.

It will be appreciated by those skilled in the art that these characteristics help to determine the salability of the foam and thus the dispenser of the foam. Specifically the foam coverage is important because if the foam covers the user's hands well it is likely that less soap will be used by each user and therefore the cost per use is less. Similarly the better the rinse characteristics the less water that is used and therefore the less the overall cost per hand wash.

Further, it will be appreciated by those skilled in the art that the term valve used herein could have a very broad definition. As is well known at its broadest a valve is a device in a pipe or an aperture that controls the passage of air, steam or liquid. Accordingly a valve may be a mechanical device as shown herein or alternatively it may be a series of weirs that control the flow of the liquid. Specifically a valve as used herein in regard to non-return valves 42, 80, 84, 108, 118 and 122 as well as elastomeric valve 158 could be replaced by weirs.

In order to provide a rating system marks were assigned to each characteristic. Specifically in regard to the bubble size a mark out of 10 was determined from the scale shown in FIG. 17. In regard to the stamina, it was decided that 20 secs of duration deserved a ten out of ten which lead to every two seconds being worth one point. Therefore 10 sec equals 5 out of 10. The pride was measured in degrees from 0-90. It was decided that an angle of 70 degrees was considered a 10 and 10 degrees was a 1. Therefore 40 degrees is 4/7 which equals 5.7 out of 10. Coverage was measured in grams and the fewer the better. It was decided that a score of zero was assigned to 3:6 grams and a score of ten was assigned to 0.6 grams. The score out of ten is calculated by the equation $x=(y-3.6)/-0.2$ which comes from the equation of a line formula $y=mx+b$, where x represents the points and y is the result in grams. The rinse was measured in grams and the fewer grams of water the better. The equation to find the value for rinse was $x=(y-375)/-25$.

A number of foam samples were tested and given five scores out of ten that were weighted and averaged to give a final percentage score. Each criterion was given a weight on how much it sways the final preference rating. Bubble size, duration and stiffness were weighted at 25%, coverage was at 15% and rinse was weighted at 10%. It will be appreciated by those skilled in the art that a score of 100 may not necessarily be the most desirable foam because it may be slightly too stiff and the bubbles too small somewhat like mousse. However in this experiment the objective was to get as close to 100, and if there were certain characteristics that may not be somewhat undesirable the design can be modified from there. One hypothesis is that the ideal foam would be near 85 on this scale.

The results from some experiments using this methodology are shown in the following table.

| Annulus (mm gap) | Bubble size (25%) | Stamina (25%) | Pride (25%) | Coverage (15%) | Rinse (10%) | Average score | Rating! |
|---|---|---|---|---|---|---|---|
| 3.2 | 3.93 | 6.00 | 5.24 | 5.8 | 7.33 | 5.66 | 53.96 |
| 2.1 | 5.97 | 3.55 | 4.90 | 5.7 | 6.79 | 5.38 | 51.39 |
| 1.2 | 4.53 | 4.08 | 5.48 | 6.3 | 7.01 | 5.48 | 51.69 |
| 0.72 | 7.53 | 4.73 | 6.00 | 5.2 | 7.72 | 6.24 | 61.19 |
| 0.065 | 7.93 | 7.25 | 6.67 | 9.3 | 7.81 | 7.79 | 76.39 |

Expenmental Results

-continued

Experimental Results

| Annulus (mm gap) | Bubble size (25%) | Stamina (25%) | Pride (25%) | Coverage (15%) | Rinse (10%) | Average score | Rating! |
|---|---|---|---|---|---|---|---|
| Mandrel (mm) | | | | | | | |
| 9.2 | 5.20 | 3.93 | 6.00 | 4.8 | 7.09 | 5.40 | 52.12 |
| *(highlighted)* | | | | | | | |
| 34.6 | 7.18 | 7.00 | 6.94 | 6.9 | 6.62 | 6.93 | 69.77 |
| 46.5 | 6.40 | 7.15 | 6.29 | 9.3 | 7.58 | 7.34 | 71.12 |
| Vertical | | | | | | | |
| Exit Nozzle Length | | | | | | | |
| *(highlighted)* | | | | | | | |
| 36 | 7.02 | 6.10 | 6.86 | 8 | 7.13 | 7.02 | 69.07 |
| 18 | 8.06 | 5.30 | 7.14 | 8.5 | 7.09 | 7.22 | 71.10 |
| 0 | 7.54 | 7.00 | 5.86 | 8.7 | 5.95 | 6.61 | 66.99 |
| Air Ratio | *(highlighted)* | | | | | | |
| Gojo hand pump | 9 | 4.83 | 8.57 | 12.2 | 7.62 | 8.44 | 81.93 |
| | 8 | 10 | 7.86 | 8 | 5.45 | 7.86 | 82.10 |
| ideal | 9.3 | 8 | 8.00 | 9 | 9 | | 85.75 |

The highlighted results are a preferred state of the variables. By using a stepped annulus we were able to be cost effective and use the 22 mm mandrel as well as decrease the chance for clogging. Placing the mixing chamber vertically helped the stepped annulus to work even better. A 55 mm exit nozzle helped produce the best foam. The characteristics of the foam improve the more it is sheared. It was assumed that the elongate exit nozzle was providing back pressure and this could be alternatively achieved by using an elastomeric valve. An air ratio of 45:1 produced foam that had a good combination of pride and bubble size. This was with a heavy duty type soap. It will be appreciated by those skilled in the art that the air to soap ratio may vary between 8:1 and 80:1. The preferred ratio will depend on the quality of foam desired and the surfactant content in the soap.

In one embodiment the porous mandrel 34 was constructed from a sintered polymer. The sintered polymer will typically have a pore size that ranges from 10 to 300 microns. Preferably the pore size is as small as practicable and this is a function of the surface tension and the relative densities of the liquid and the mandrel material. The length of the mandrel ranges from 9 to 47 mm. The diameter of the mandrel ranges from 5-20 mm. In one embodiment the mandrel has a diameter of 12.65 mm, a length of 22 mm and a pore size of 100 microns.

The gap between the mandrel and the outside wall of the foaming component or the width of the annular mixing chamber ranges from 0.06 to 3.5 mm. Generally, the smaller the width of the annulus the better the quality of foam. However, this design constraint must be balanced against the risk of the clogging and generally the smaller the width of the annulus the higher the risk of clogging. Empirically, it was determined that the minimum width of the annular mixing chamber is 1.5 times the size of the particles when using a 7% particles to soap ratio by weight. Generally if the annulus is smaller than 1.5 times the particle size, the particles will clog. Further if the concentration of particles is increased, the particles will clog unless the width of the annulus is increased. Generally the foam quality is reduced if the width of the annulus is increased, however empirically it was determined that the best results were achieved when the width of the annulus is at 8 times the particle size using a 7% particles to soap ratio by weight. It was also determined that a stepped annulus produced good quality foam. In the stepped annulus embodiment similar to that shown in FIG. 12, the width of the annular mixing chamber is 3.2 mm along the first 10 mm of the mandrel and then the width becomes 0.7 mm for the last 12 mm. Using this technique, it was determined that the stepped annular mixing chamber produced better quality foam using a 22 mm mandrel compared to a 46.5 mm mandrel with a constant width annular mixing chamber. Preferably the width of the annular mixing chamber remains constant in the different sections of the mixing chamber. That is, the shape of the mixing chamber, particularly around the end of the mandrel, follows the contour of the mandrel.

Further, it was empirically noted that the best foam was produced using a long exit nozzle. Specifically based on the experiments conducted the best performance was achieved from a 55 mm length exit nozzle that was 5 mm in diameter. Alternatively an elastomeric valve can be used to create a comparable back pressure. It was also noted that the best results were achieved when the foaming component is oriented vertically instead of horizontally. However, this may be difficult to accommodate within the footprint of conventional dispensers.

It will be appreciated by those skilled in the art that a wide variety of soaps and combinations of soap and particles may be used with the present invention. Generally. any foamable liquid may be foamed using the dispenser of the present invention. In regard to the particles, a wide variety of particles may be used. Some examples of particles include pumice, cornmeal, ground walnut shells, ground fruit stones, wood flour, microcapsules, microbeads (polyethylene, polypropylene etc.), and dried pulses (peas etc.). Typically the microbeads float, while the others listed types of particles sink. These are the types of particles that are used as abrasives in soaps for use on heavily soiled skin or for exfoliating. Alternatively other particles could be used for other purposes. For example the particles may be microcapsules that when broken release a fragrance, or microcapsules that have an active constituent that is unstable such that when it is broken an exothermic reaction takes place and the foam will be a heated foam. Whether the particles float or sink or stay in suspension depends on the rheological properties of the liquid. Non-Newtonian liquids/gels with a yield value (such as Casson and Bingham fluids) have suspending properties which do not depend on viscosity or density. Generally the percentage of particles in the foam will not affect the quality of the foam. The percentage of particles in the foam can vary greatly and would be dependent on the particular use. Generally the percentage of particles by weight will vary from 1% to 20% and will be dependent on the requirements of the particular market, the characteristics of the foam and the type and size of the particles. The size of the particles may vary and an appropriate size should be chosen to provide the desired "feel". Generally the size of the particle is linked to its surface roughness and to its hardness. Hard mineral particles such as silica, calcium carbonate etc. are generally preferably between 90 and 130 microns. Organic particles such as corn meal are generally preferably at a higher granulometry of between 200 and 700 microns because they are softer. Generally particles will range from 90 to 700 microns. Generally the viscosity of the liquid can range from 2 centipose at 25 degrees C. to 100 centipose at 25 degrees C., wherein the liquid is a liquid with or without particles therein.

When considering the above dispensers for dispensing foam with particles suspended therein, there are potentially four different types of liquids that are used for inputs. Specifically, liquids wherein the particles tend to float, liquids wherein the particles tend to sink, liquids wherein the particles are suspended throughout and two liquids which are released generally at the same time into the liquid conduit prior to being dispensed. In addition, there is the embodiment wherein the liquid is agitated in the liquid container prior to being released into the liquid conduit.

In regard to the alternative wherein there is one liquid input, the liquid may include the following ingredients: water, surfactants (non-ionics and/or anionics and/or amphoterics and/or cationics), at least one non-Newtonian thickener with significant yield value (acrylic and/or acrylate-based polymers and copolymers, natural gums, pyrogenated silica, clay, bentonites and their derivatives or combinations), at least one preservative (able to prevent the growth of bacteria, yeasts and molds), solvent(s) (terpenes, hydrocarbon-based solvents, esters, ethers, alcohols, glycols etc.). It may also contain some emollients/moisturisers (polyols, plyethylene glycol derivates, fatty esters, fatty alcohols, fatty acids, glycerides, triglycerides etc.), pH-adjuster (acis or alkali). As well, it may also contain some cosmetic additives such as perfume, colouring dyes etc. These liquids could be used in association with pumice, cornmeal, ground walnut shells, ground fruit stones, wood flour, microcapsules, microbeads (polyethylene, polypropylene etc.), and dried pulses (peas etc.). The appropriate dispenser is chosen dependent on the characteristics of the liquid and particle input. The two liquid system may have similar ingredients distributed between the two liquids.

In regard to the alternative using two liquid, the fist liquid is a high viscosity liquid with the particles suspended therein and the second liquid when mixed with the first liquid provides a liquid with a viscosity generally between 2 centipose at 25° C. to 100 centipose at 25 ° C. The high viscosity liquid may have a water base. It may further include cleaning agents such as surfactants, emollients, humectants, solvents, cosmetic ingredients or a combination thereof and an appropriate thickener such as carbomers, natural and synthetic gums or a combination thereof. The low viscosity diluents may contain water, additional cleaners, surfactants, electrolytes or other desirable ingredients that would reduce the high viscosity cleanser or combinations thereof. The percentage of particles in the high viscosity liquid is chosen such that once mixed with the second liquid the percentage of particles is between 1% and 20% by weight of the resulting foam.

The proportion of mixing the two parts can be varied to suit the needs of the particular formulation, but would typically be from 20:80 to 80:20. Each part could contain various parts of the desired final foam, such as cleansers, conditioners, emollients, fragrances, colours. The preferred proportion is 50:50 for ease of handling.

The ingredients for the two liquids are chosen such that when combined the viscosity of the combination will range from 2 centipose at 25 degrees C. to 100 centipose at 25 degrees C. The change in viscosity when the two liquids are mixed can be achieved by dilution, by varying the pH or by modifying the electrolyte content. Generally dilution will work for most thickeners.

Alternatively, by changing the pH of the suspension liquid by mixing with the diluent liquid, an appropriate viscosity for the foamable mixture may be obtained. This approach will work with a select type of thickeners. These thickeners require a predetermined pH or range of pH to thicken a liquid and if pH of the liquid falls outside that range the thickener no longer acts as a thickener. Accordingly, such a thickener may be used in the high viscosity liquid with the particles suspended therein and an acid may be used in the low viscosity liquid. Therefore on mixing the pH will be lowered so that the mixture is outside the effective range for the thickener and thus an acceptable viscosity for making foam is achieved. Carbomers are an example of such thickeners and they could be used in association with a suitable physiologically acceptable acid such as citric acid. Generally, an acrylic acid-based thickener such as carbomer and a solution of electrolyte sodium chloride is the preferred system. Once both ingredients are mixed together, the electrolyte will reduce the thickeners Zeta potential and will disorganise irreversibly its three dimensional network and therefore the viscosity will drop. It will be appreciated by those skilled in the art that system wherein the viscosity drop is achieved within an acceptable time frame should be chosen.

Similarly the desired viscosity of the mixture of the first and second liquids may be obtained by modifying the electrolyte content. For example methyicellulose when in a solution with low electrolyte will exhibit thickening characteristics but when mixed such that the new solution has a high electrolyte content the viscosity lowers or breaks down. A sodium chloride solution may be used in the second liquid to raise the electrolyte content. Another calcium salts and metals may be used in the second liquid to raise the electrolyte content.

The type of strategy or method to use in order to achieve the right mixture will be entirely dependant upon the Industrial Cleaner composition and which thickener is used in it to then decide what is the best approach to dilute to the required viscosity in order to foam.

It will be clear to those skilled in the art that there are a number of variations that may be made while being within the scope of the patent. Specifically the liquid containers may be either rigid or collapsible. The dispenser may be used with soap, a soap and particles mixture, or soap and a high concentration of particles in separate containers. The liquid which includes particles may have the particles suspended therein. Alternatively the dispenser may be designed to work with particles that sink or particles that float.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A foaming component for use in association with a foam skin care dispenser, comprising:
    a microporous air sparging element having an upstream end and a downstream end defining a length thereof;
    a mixing chamber adjacent the microporous air sparging element and on a first side of the microporous air sparging element and a first surface of the microporous air sparging element defining a portion of the mixing chamber and the mixing chamber having a foamable liquid inlet adjacent the upstream end of the microporous air sparging element;
    an air chamber adjacent the microporous air sparging element and on a second side of the microporous air sparging element and a second surface of the microporous air sparging element defining a portion of the air chamber and the air chamber having an air inlet adjacent the upstream end of the microporous air sparging element;
    a mixing chamber outlet downstream of the foamable liquid inlet in the mixing chamber wherein the mixing chamber outlet is spaced downstream from the foamable liquid inlet along at least a portion of the length of the air sparging element; and
    user activated pump means for concurrently forcing a predetermined ratio of air and a foamable liquid through the air inlet and the foamable liquid inlet, respectively, the predetermined ratio having a greater proportion of air to foamable liquid, such that the foamable liquid is forced into the mixing chamber, and such that air is forced into the air chamber and through the microporous air sparging element to form a plurality of bubbles in the foamable liquid, whereby a density of the plurality of bubbles in the foamable liquid increases from the liquid inlet to the liquid outlet in the mixing chamber to form a foamed liquid that is dispensed to the user in shots from a nozzle positioned downstream of the mixing chamber outlet, wherein the foamable liquid includes a plurality of particles having a predetermined average diameter and at least one non-Newtonian thickener, the foamable liquid exhibiting viscosity at low shear rates that is sufficient to maintain particles suspended therein and has low viscosity when exposed to high shear rates,
    wherein the microporous air sparging element is generally a test tube shape and the mixing chamber is generally an elongate annular tube defining an annular gap being the difference in length between an outer radius of the test tube shape and an outer radius of the elongate annular tube, wherein a width of the annular gap is 1.5 to 8 times the average diameter of the plurality of particles.

2. A foaming component as claimed in claim 1 wherein the mixing chamber outlet is a nozzle.

3. A foaming component as claimed in claim 2 wherein the nozzle is an elongate nozzle.

4. A foaming component as claimed in claim 3 wherein the nozzle has a valve positioned therein.

5. A foaming component as claimed in claim 4 wherein the valve is an elastomeric valve.

6. A foaming component as claimed in claim 1 wherein the foaming component is oriented vertically.

7. A foaming component as claimed in claim 1 wherein the foaming component is oriented horizontally.

8. A foaming component as claimed in claim 1 wherein the width of the annular tube is 1.5 times the average diameter of the plurality of particles.

9. A foaming component as claimed in claim 1 wherein the width of the annular tube is 0.06 to 3.5mm.

10. A foaming component as claimed in claim 9 wherein the length of the microporous air sparging element is 9 to 47 mm.

11. A foaming component as claimed in claim 10 wherein the diameter of the microporous air sparging element is 5 to 20 mm.

12. A foam skin care dispenser for use in association with a foamable liquid, comprising:
    a housing
    at least one foamable liquid container positioned in the housing;
    a user activated pump device including a foamable liquid chamber and an air chamber and further including means for concurrently applying pressure to discharge foamable liquid from the foamable liquid chamber and air from the air chamber;
    a foaming component including:
        a microporous air sparging element having an upstream end and a downstream end defining a length thereof;
        a mixing chamber adjacent the microporous air sparging element and on a first side of the microporous air sparging element and a first surface of the microporous air sparging element defining a portion of the mixing chamber and the mixing chamber having a foamable liquid inlet adjacent the upstream end of the microporous air sparging element which inlet is in flow communication with the foamable liquid chamber;
        a foaming component air chamber adjacent the microporous air sparging element and on a second side of the microporous air sparging element and a second surface of the microporous air sparging element defining a portion of the air chamber and the air chamber having an air inlet adjacent the upstream end of the microporous air sparging element in communication with the air chamber;
        a mixing chamber outlet downstream of the foamable liquid inlet in the mixing chamber wherein the mixing chamber outlet is spaced downstream from the foamable liquid inlet along at least a portion of the length of the air sparging element; and the pump device being operable to concurrently pump a predetermined ratio of air and the foamable liquid into the foaming component air chamber and the mixing chamber respectively, the predetermined ratio having a greater proportion of air to foamable liquid, such that air is forced into the air chamber and through the microporous air sparging element forming a plurality of bubbles in the foamable liquid, whereby a density of the plurality of bubbles in the foamable liquid increases from the liquid inlet to the liquid outlet in the mixing chamber to form foam and so as to discharge shots of foam from an outlet of the dispenser to the user, wherein the foamable liquid includes a plurality of particles having a predetermined average diameter, the foamable liquid exhibiting viscosity at low shear rates that is sufficient to maintain particles suspended therein and has low viscosity when exposed to high shear rates, wherein the microporous air sparging element is generally a test tube shape and the mixing chamber is generally an elongate annular tube defining an annular gap being the difference in length between an outer radius of the test tube shape and an outer radius of the elongate annular tube, wherein a width of the annular gap is 1.5 to 8times the average diameter of the plurality of particles.

13. A foam dispenser as claimed in claim 12 wherein the foamable chamber has an inlet in flow communication with the foamable liquid container and an outlet in flow communication with the mixing chamber of the foaming component, the foamable liquid chamber having an interior volume which changes responsive to an actuation means; and the air chamber having an air inlet and an outlet, the outlet being in flow communication with the foaming component air chamber, and the air chamber has an interior volume which changes responsive to an actuation means.

14. A foam dispenser as claimed in claim 13 wherein the foamable liquid chamber and the air chamber are portions of piston type pumps and the liquid chamber and air chamber discharge predetermined ratios of liquid from the liquid chamber and air from the air chamber.

15. A foam dispenser as claimed in claim 13 wherein the foamable liquid chamber and the air chamber are portions of diaphragm type pumps and the foamable liquid chamber and air chamber discharge predetermined ratios of foamable liquid from the liquid chamber and air from the air chamber.

16. A foam dispenser as claimed in claim 12 wherein the foamable liquid includes particles that tend to sink to form a sediment in the bottom of the foamable liquid container and further including a puck loading system whereby a predetermined amount of sediment is added to the foamable liquid in the foamable liquid chamber.

17. A foam dispenser as claimed in claim 16 wherein the foamable liquid container has an interior, an opening and a throat proximate to the opening and a cap having a puck aperture and a foamable liquid aperture, a foamable liquid tube extends upwardly into the interior of the foamable liquid container, the cap is positioned in the throat and wherein the puck loading system includes a rotatable skim and loading wheel, the skim and loading wheel having a plurality of spaced apart apertures formed therein, the apertures being generally at the same radius, the skim and loading wheel is positioned in the throat of the foamable liquid container such that the apertures in the skim and loading wheel are selectively in registration with the puck aperture and the liquid aperture in the cap, whereby rotation of the skim and loading wheel moves one of the plurality of apertures from in registration with the puck aperture to in registration with the liquid aperture.

18. A foam dispenser as claimed in claim 12 wherein the foamable liquid container is a first liquid container and further including a second liquid container and wherein the first and second containers are in flow communication with the mixing chamber liquid inlet.

19. A foam dispenser as claimed in claim 18 wherein the first liquid container is in flow communication with the liquid chamber and further including a liquid conduit extending between the liquid chamber and the mixing chamber liquid inlet and the second container is in flow communication with the liquid container.

20. A foam dispenser as claimed in claim 19 further including a venturi in the liquid conduit between the liquid container a position downstream thereof where the second liquid container flows into the liquid conduit.

21. A foam dispenser as claimed in claim 20 wherein the first liquid container is in flow communication with the liquid chamber and further including a liquid conduit extending between the liquid chamber and the mixing chamber liquid inlet and the second container is in flow communication with the liquid container.

22. A foam dispenser as claimed in claim 12 wherein the pump includes:
a first liquid chamber having an inlet in flow communication with the first liquid container and an outlet in flow communication with the mixing chamber of the foaming component, the first liquid chamber having an interior volume which changes responsive to an actuation means;
a second liquid chamber having an inlet in flow communication with a second liquid container and an outlet in flow communication with the mixing chamber of the foaming component, the second liquid chamber having an interior volume which changes responsive to an actuation means; and
an air chamber having an air inlet and an outlet the outlet being in flow communication with the microporous air sparging element air chamber, and the air chamber has an interior volume which changes responsive to an actuation means.

23. A foam dispenser as claimed in claim 22 wherein the first liquid container contains the foamable liquid and the second liquid container contains a liquid with a high concentration of particles.

24. A foam dispenser as claimed in claim 23 wherein the particles are chosen from a group consisting of pumice, cornmeal, ground walnut shells, ground fruit stones, wood flour, microbeads, microcapsules, dried pulses and a combination thereof.

25. A foam dispenser as claimed in claim 12 further including an agitator mechanism operably contained in the liquid container and operably connected to an actuation means whereby responsive to the actuation means the liquid in the liquid container is mixed.

26. A foam dispenser as claimed in claim 25 wherein the agitator mechanism includes a motor connected to a power supply and an agitator device operably connected to the motor and extending into the liquid container.

27. A foam dispenser as claimed in claim 26 wherein the power supply is a pair of batteries.

28. A foam dispenser as claimed in claim 12 wherein the liquid includes particles that tend to float to the top of the liquid, the liquid container is an inverted liquid container and has a liquid outlet and further including a skimming mechanism operably connected to an actuation means whereby the particles are skimmed from the top of the liquid and moved to the liquid outlet responsive to the actuation means.

29. A foam dispenser as claimed in claim 28 wherein the skimming mechanism includes an auger extending upwardly from the liquid outlet to a top of the liquid container and a sleeve extending upwardly into the liquid container and positioned around the auger and upwardly from the liquid outlet.

30. A foam dispenser as claimed in claim 12 wherein the liquid includes particles that tend to sink to the bottom of the liquid, the liquid container is an upright liquid container and has a liquid outlet and further including an auger mechanism operably connected to an actuation means whereby the particles are scooped from the bottom of the liquid and moved to the liquid outlet responsive to the actuation means.

31. A foam dispenser as claimed in claim 30 wherein the auger mechanism includes an auger extending downwardly from the liquid outlet to a top of the liquid container and a sleeve extending upwardly into the liquid container and positioned around the auger and upwardly from the liquid outlet.

32. A foam dispenser as claimed in claim 12 wherein the container is a collapsible container.

33. A foam dispenser as claimed in claim 13 wherein the container is a rigid container.

34. A foam dispenser as claimed in claim 13 wherein the container is inverted.

35. A foam dispenser as claimed in claim 13 wherein the container is upright.

36. A method of making skin care foam including the steps of:
introducing a predetermined quantity of air under pressure to a first side of and adjacent an upstream end of a microporous air sparging element;
introducing, concurrently with the introduction of the air, a predetermined amount of a foamable liquid under pressure to a foamable liquid inlet of a mixing chamber, the mixing chamber being adjacent to the microporous air sparging element and on a second side of the microporous air sparging element and foamable liquid inlet being adjacent to the upstream end of the microporous air sparging element, such that a ratio of air to foamable liquid has a greater proportion of air to foamable liquid;
forcing the air through the microporous sparging element into the mixing chamber to form a plurality of bubbles;
mixing the plurality of bubbles and the foamable liquid in the mixing chamber thereby creating foam; and
dispensing the foam to a user in shots through an outlet from the mixing chamber, the outlet being spaced downstream from the foamable liquid inlet,
wherein the foamable liquid includes a plurality of particles having a predetermined average diameter, the foamable liquid exhibiting viscosity at low shear rates that is sufficient to maintain particles suspended therein and has low viscosity when exposed to high shear rates, and wherein the microporous air sparging element is generally a test tube shape and the mixing chamber is generally an elongate annular tube defining an annular gap being the difference in length between an outer radius of the test tube shape, wherein a width of the annular gap is 1.5 to 8 times the average diameter of the plurality of particles.

37. A method as claimed in claim 36 further including the step of mixing a liquid with a high concentration of particles with a liquid with generally no particles upstream of providing the liquid under pressure to the mixing chamber.

38. A method as claimed in claim 36 wherein the air is introduced in a predetermined quantity and the foamable liquid is introduced in a predetermined quantity.

* * * * *

UNITED STATES PATENT AND TRADEMARK OFFICE
Certificate

Patent No. 8,002,151 B2                                                    Patented: August 23, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Shaun Kerry Matthews, Lincoln (GB); Stewart Banks, Algarve (PT); Kara Catherine Stonehouse, Kanata (CA); Pierre Bruno Grascha, Cormontreuil (FR); Cynthia Louise Grimadell, Derbyshire (GB); and Elizabeth Ann Bowley, Derbyshire (GB).

Signed and Sealed this Thirteenth Day of May 2014.

*PAUL R. DURAND*
*Supervisory Patent Examiner*
*Art Unit 3754*
*Technology Center 3700*